United States Patent [19]

Iwane et al.

[11] Patent Number: 5,858,779
[45] Date of Patent: *Jan. 12, 1999

[54] MONOCLONAL ANTIBODY, HYBRIDOMA, THEIR PRODUCTION AND USE THEREOF

[75] Inventors: Makoto Iwane, Suita; Tsutomu Kurokawa, Kawanishi; Koichi Igarashi, Kyoto, all of Japan

[73] Assignee: Takeda Chemical Industries, Ltd., Osaka, Japan

[*] Notice: The term of this patent shall not extend beyond the expiration date of Pat. No. 5,478,740.

[21] Appl. No.: 567,748

[22] Filed: Dec. 5, 1995

Related U.S. Application Data

[62] Division of Ser. No. 915,025, Jul. 15, 1992, Pat. No. 5,478,740, which is a continuation of Ser. No. 157,453, Feb. 18, 1988, abandoned.

[30] Foreign Application Priority Data

Mar. 3, 1987 [JP] Japan .................. 62-49759
Aug. 26, 1987 [JP] Japan .................. 62-211599
Jan. 26, 1988 [JP] Japan .................. 63-16260

[51] Int. Cl.$^6$ .............. C12N 5/12; C07K 16/26; C07K 16/18
[52] U.S. Cl. ............ 435/336; 530/388.24; 530/388.1
[58] Field of Search .............. 530/388.24, 387.1, 530/388.1; 435/325, 336

[56] References Cited

PUBLICATIONS

Seno, M. et al, Hybridoma, 8(2):209–221, 1989.
Abraham, J.A. et al, Embo Journal, 5(10):2523–2528, 1986.
Massoglia, S.L. et al, J. Cellular Physiol, 132:531–537, 1987.
Moscatelli, D. et al, J. Cell Physiol, 129:273–276, 1986.

*Primary Examiner*—Susan A. Loring
*Attorney, Agent, or Firm*—David G. Conlin; Ronald I. Eisenstein; Dike, Bronstein, Roberts & Cushman, LLP

[57] ABSTRACT

A monoclonal antibody is produced from a cloned hybridoma, and the monoclonal antibody combines specifically with basic fibroblast growth factor (bFGF). Therefore, the monoclonal antibody can be advantageously used for assay reagents on bFGF or for purification of bFGF.

4 Claims, 8 Drawing Sheets

ProAlaLeuProGluAspGlyGlySerGlyAlaPheProProGlyHisPheLysAsp
CCAGCATTGCCCGAGGATGGCGGGCAGCGGCCCTTCCCGCCCGGCCACTTCAAGGAC

ProLysArgLeuTyrCysLysAsnGlyGlyPheLeuArgIleHisProAspGlyArg
CCCAAGCGGCTGTACTGCAAAAACGGGGGCTTCTTCCTGCGCATCCACCCGACGGCCGA

ValAspGlyValArgGluLysSerAspProHisIleLysLeuGlnLeuGlnAlaGluGlu
GTTGACGGGGTCCGGGAGAGACGACCCTCACATCAAGCTACAACTTCAAGCAGAAGAG

ArgGlyValValSerIleLysGlyValCysAlaAsnArgTyrLeuAlaMetLysGluAsp
AGAGGAGTTGTCTATCAAAGGAGTGTGCTAACCGTTACCTGGCTATGAAGGAAGAT

GlyArgLeuLeuAlaSerLysCysValThrAspGluCysPhePheGluArgLeuGlu
GGAAGATTACTGGCTTCTAAATGTGTTACGGATGAGTGTTTCTTTTTGAACGATTGGAA

SerAsnAsnTyrAsnThrTyrArgSerArgLysTyrThrSerTrpTyrValAlaLeuLys
TCTAATAACTACAATACTTACCGGTCAAGGAAATACACCAGTTGGTATGTGGCACTGAAA

ArgThrGlyGlnTyrLysLeuGlyLysSerThrGlyProGlyGlnLysAlaIleLeuPhe
CGAACTGGGCAGTATAAACTTGGATCCAAAACAGGACCTGGGCAGAAAGCTATACTTTTT

LeuProMetSerAlaLysSer
CTTCCAATGTCTGCTAAGAGC

FIG. 1

MONOCLONAL ANTIBODY, HYBRIDOMA, THEIR PRODUCTION AND USE THEREOF

This is a divisional of application Ser. No. 07/915,025 filed Jul. 15, 1992, now U.S. Pat. No. 5,478,740 which is a continuation of Ser. No. 07/157,453, filed on Feb. 18, 1988, now abandoned.

The present invention relates to monoclonal antibodies which combine specifically with basic fibroblast growth factor, hybridomas, their production and use thereof.

The basic fibroblast growth factor (also briefly referred to as bFGF, in the present specification) is a basic polypeptide hormone which is secreted mainly from the pituitary gland and which has a molecular weight of about 17,000. It was first isolated as a factor showing potent growth promoting action on fibroblasts such as BALB/C3T3 cells [D. Gospodarowicz: Nature, 249, 123 (1974)]. Later, however, it was revealed that it exhibits growth promoting action on almost all mesoderm-derived cells [D. Gospodarowicz et al.: National Cancer Institute Monograph, 48, 109 (1978)]. The neo-vascularizing activity of bFGF, among others, conjointly with its cell growth promoting activity, suggests the possibility of its use as a therapeutic agent for lesions and burns and as a preventive/therapeutic agent for thrombosis, arteriosclerosis and the like.

The quantity of naturally occurring human bFGF is very small, and attempts to obtain this factor from human tissues have encountered serious difficulties arising from various restrictions and limitations. In addition, any method that is easily usable for quantitative determination of bFGF has not been established to date. For these reasons, much remains unknown of basic information which is essential for developing bFGF as a drug, such as the properties of bFGF.

Therefore, the development of bFGF as a drug will be facilitated if further basic information about bFGF is known, for example, the distribution of bFGF in vivo and the manner of its production.

In addition, to accurately determine the quantity of bFGF is important in purifying this protein from gene recombinants. Moreover, it is very important to trace blood FGF concentration in animals which have had bFGF administered thereto, but blood bFGF cannot be determined by the conventional method using 3T3 cells, due to the mingling of serum in the sample. Usually, the determination of bFGF is achieved by adding bFGF to 3T3 cells which have been cultured at reduced serum concentration to attenuate their DNA synthesizing potency, and counting back bFGF concentration from the degree of recovery of DNA synthesizing potency. However, this method is faulty in that the procedure is delicate and determination errors are great, due to the use of cells, and in addition much time is needed to obtain results. It is therefore desired that a simple and accurate means of bFGF determination will be developed for the above-mentioned purpose.

Taking note of the above-mentioned circumstances, the present inventors made various investigations to find any practical means of bFGF determination, and prepared a monoclonal antibody which combines specifically with bFGF and which enables the determination thereof. The present inventors conducted further researches based on this achievement, and as a result have now developed the present invention.

The present invention provides:

(1) a monoclonal antibody which combines specifically with basic fibroblast growth factor (bFGF), the monoclonal antibody having the characteristics:
 (a) it has a molecular weight of about 140 to 160 kilodaltons,
 (b) it does not cross-react with acidic fibroblast growth factor, and
 (c) it belongs to the immunoglobulin class IgM or IgG;

(2) a cloned hybridoma comprising a splenic cell from a mammal immunized with bFGF and a homogenic or heterogenic lymphoid cell;

(3) a method for producing a cloned hybridoma comprising a splenic cell from a mammal immunized with bFGF and a homogenic or heterogenic lymphoid cell, which comprises subjecting said splenic cell and said lymphoid cell to cell fusion followed by cloning;

(4) a method for producing a monoclonal antibody which combines specifically with bFGF, which comprises growing a cloned hybridoma comprising a splenic cell from a mammal immunized with said factor and a homogenic or heterogenic lymphoid cell in liquid medium or mammalian abdomen to allow the hybridoma to produce and accumulate the monoclonal antibody;

(5) a method for purifying bFGF, which comprises treating a material containing crude bFGF with the use of the monoclonal antibody defined in said item (1); and (6) a method for detecting or measuring bFGF, which comprises using, as antibody, the monoclonal antibody defined in said item (1).

As the bFGF for immunizing mammals, any bFGF can be included, as long as it is a bFGF of a warm-blooded mammal. Its mutein can also be used, so in the present specification "basic fibroblast growth factor (bFGF)" may include its mutein unless otherwise specified.

As representative examples of such mammalian bFGF, mention may be made of bovine bFGF [Proceedings of the National Academy of Sciences, U.S.A., 82, 6507 (1985)] and human bFGF [Japanese Patent Application No. 241053/1986 which corresponds to European Patent Publication No. 237,966; European Molecular Biology Organization (EMBO) Journal, 5, 2523 (1986)].

Polypeptides which includes the amino acid sequence:

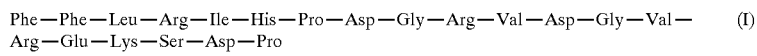

Phe—Phe—Leu—Arg—Ile—His—Pro—Asp—Gly—Arg—Val—Asp—Gly—Val—  (I)
Arg—Glu—Lys—Ser—Asp—Pro are preferred.

More preferably, the polypeptides are represented by the formula:

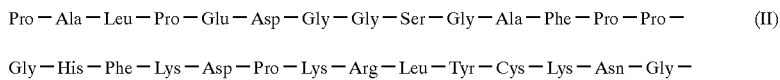

Pro—Ala—Leu—Pro—Glu—Asp—Gly—Gly—Ser—Gly—Ala—Phe—Pro—Pro—  (II)
Gly—His—Phe—Lys—Asp—Pro—Lys—Arg—Leu—Tyr—Cys—Lys—Asn—Gly—

-continued

Gly—Phe—Phe—Leu—Arg—Ile—His—Pro—Asp—Gly—Arg—Val—Asp—Gly—

Val—Arg—Glu—Lys—Ser—Asp—Pro—His—Ile—Lys—Leu—Gln—Leu—Gln—

Ala—Glu—Glu—Arg—Gly—Val—Val—Ser—Ile—Lys—Gly—Val—Cys—Ala—

Asn—Arg—Tyr—Leu—Ala—Met—Lys—Glu—Asp—Gly—Arg—Leu—Leu—Ala—

Ser—Lys—Cys—Val—Thr—Asp—Glu—Cys—Phe—Phe—Phe—Glu—Arg—Leu—

Glu—Ser—Asn—Asn—Tyr—Asn—Thr—Tyr—Arg—Ser—Arg—Lys—Tyr—X—Ser—

Trp—Tyr—Val—Ala—Leu—Lys—Arg—Thr—Gly—Gln—Tyr—Lys—Leu—Gly—Y—

Lys—Thr—Gly—Pro—Gly—Gln—Lys—Ala—Ile—Leu—Phe—Leu—Pro—Met—Ser—

Ala—Lys—Ser wherein X represents Thr or Ser; Y represents Ser when X is Thr or Y represents Pro when X is Ser.

For obtaining human bFGF (also briefly referred to as hbFGF), an expression vector which contains a DNA segment having a base sequence encoding, for example, the above-mentioned hbFGF protein polypeptide, can be produced, for example, by:

(a) Isolating an RNA encoding hbFGF;

(b) Synthesizing from said RNA a single-stranded complementary DNA (cDNA) and then a double-stranded DNA;

(c) Inserting said complementary DNA into a plasmid;

(d) Transforming a host with the resultant recombinant plasmid;

(e) Cultivating the transformant thus obtained, then isolating the plasmid which contains the desired DNA from the transformant by an appropriate method, for example, the colony hybridization method using a DNA probe;

(f) Cleaving off the desired cloned DNA from said plasmid; and (g) Inserting said cloned DNA into a vehicle at a site downstream from a promoter.

RNAs encoding hbFGF can be obtained from a wide variety of hbFGF-producing cells such as human pituitary-derived cells or human fibroblasts. Such human fibroblasts include WI38 (ATCC No. CCL-75) and IMR90 (ATCC No. CCL-186). Said cell lines WI38 and IMR90 are listed in the Catalogue of Cell Lines & Hybridomas, 5th edition, 1985, published by the American Type Culture Collection.

By inserting the expression vector thus obtained into an appropriate host (e.g., Escherichia coli, Bacillus subitlis, yeasts, animal cells), and cultivating the obtained transformant in a medium, human bFGF can be produced.

The muteins in the present invention essentially have the amino acid sequence of the original peptide or protein; but variations include an addition of amino acid(s), deletion of constituent amino acid(s) and substitution of constituent amino acid(s) by other amino acid(s).

Such addition of amino acid includes addition of at least one amino acid. Such deletion of constituent amino acid includes deletion of at least one bFGF-constituent amino acid. Such substitution of constituent amino acid by other amino acids includes substitution of at least one bFGF-constituent amino acid by other amino acid.

The at least one amino acid in the mutein which has at least one amino acid added to bFGF excludes methionine deriving from initiation codon used for peptide expression and signal peptide.

The number of added amino acids is at least 1, but it may be any one, as long as bFGF characteristics are not lost. Preferable amino acids should include some or all of the amino acid sequences of proteins which have homology with bFGF and which exhibit activities similar to those of bFGF.

As for the number of deleted bFGF-constituent amino acids in the present mutein which lacks at least one bFGF-constituent amino acid, it may be any one, as long as any characteristic of bFGF is not lost.

Examples of such deleted constituent amino acids include: the deletion of amino acids from amino terminal or carboxyl terminal; the deletion of the 10 residues in the amino terminal of human bFGF:

Met—Pro—Ala—Leu—Pro—Glu—Asp—Gly—Gly—Ser the 14 residues in the amino terminal of human bFGF:

Met—Pro—Ala—Leu—Pro—Glu—Asp—Gly—Gly—Ser—Gly—Ala—Phe—Pro the 41 residues in the amino terminal of human bFGF:

$$\begin{matrix} 1 & 2 & 3 & 4 & & 41 \\ Met-Pro-Ala-Leu- & \ldots & -Val \end{matrix}$$

or the 61 residues in the carboxyl terminal of human bFGF:

$$\begin{matrix} 87 & 88 & & 146 & 147 \\ Lys-Cys- & \ldots & -Lys-Ser \end{matrix}$$

As for the number of bFGF-constituent amino acids that may be substituted by other amino acids before substitution in mutein is lost, it may be any number, as long as any characteristic of bFGF is not lost.

As examples of constituent amino acids before substitution, mention may be made of cysteine and other amino acids but cysteine is preferable. As the constituent amino acid other than cysteine which may be substituted for, examples include but are not limited to aspartic acid, arginine, glycine, serine, valine and so forth.

When the constituent amino acid before substitution is cysteine, the substituted amino acids are preferably, for example, neutral amino acids. As specific examples of such neutral amino acids, mention may be made of glycine, valine, alanine, leucine, isoleucine, tyrosine, phenylalanine, histidine, tryptophan, serine, threonine and methionine. Serine and threonine are preferable.

When the constituent amino acid before substitution is other than cysteine, the substituted amino acids are selected from amino acids which are different from the amino acid before substitution in a property such as hydrophilicity, hydrophobicity or electric charge.

When the constituent amino acid before substitution is aspartic acid, examples of the substituted amino acids include asparagine, threonine, valine, phenylalanine and arginine; asparagine and arginine are preferable.

When the constituent amino acid before substitution is arginine, examples of the substituted amino acids include glutamine, threonine, leucine, phenylalanine and aspartic acid; glutamine is preferable.

When the constituent amino acid before substitution is glycine, examples of the substituted amino acids include threonine, leucine, phenylalanine, serine, glutamic acid, and arginine; threonine is preferable.

When the constituent amino acid before substitution is serine, examples of the substituted amino acids include methionine, alanine, leucine, cysteine, glutamine, arginine and aspartic acid; methionine is preferable.

When the constituent amino acid before substitution is valine, examples of the substituted amino acids include serine, leucine, proline, glycine, lysine, and aspartic acid; serine is preferable.

The constituent amino acid before substitution are preferably aspartic acid, arginine, glycine, serine and valine.

The substituted amino acid is preferably asparagine, glutamine, arginine, threonine, methionine, serine, and leucine.

The embodiment on the substitution in the mutein wherein there is a substitution of serine for cysteine (i.e. cysteine is replaced by serine) is most preferred.

In said substitution, there may be at least 2 substitutions and two or three substitutions are preferred.

The muteins in the present invention include combination of 2 or 3 of the above-mentioned additions, deletions and substitutions.

For producing said muteins, site-directed mutagenesis is carried out. This technique is well-known, and is described in Lather, R. F. and Lecoq, J. P., Genetic Engineering, Academic Press (1983), pp. 31–50. Mutagenesis which is directed to oligonucleotide is described in Smith, M. and Gillam, S., Genetic Engineering: Principles and Methods, Prenam Press (1981), vol. 3, pp. 1–32.

For producing a structural gene encoding said mutein, for example:

(a) a single-stranded DNA consisting of a single strand of a structural gene of bFGF is hybridized with a mutant oligonecleotide primer (the above-mentioned primer is complementary to a region including the cysteine codon to be replaced by this single strand or, as the case may be, an antisense triplet which forms a pair with this codon, except that discrepancies with codons for amino acid coding other than the relevant codon or, as the case may be, with antisense triplets are permitted.), (b) the primer is elongated by DNA polymerase to allow it to form a mutational heteroduplex, and (c) this mutational heteroduplex is replicated.

The phage DNA carrying the mutated gene is then isolated and inserted into a plasmid.

The plasmid thus obtained is used to transform an appropriate host (as mentioned above), and the resulting transformant is cultured in a medium, whereby mutein can be produced.

In immunizing said bFGF, the bFGF may be prepared in a complex form with a carrier protein before use.

Such carrier proteins include, for example, Freund's complete adjuvant (Difco Laboratories).

When a carrier protein complex is used, the coupling ratio of carrier protein to bFGF is about 5 to 30 times (carrier/bFGF, ratio by weight). It is preferable that the ratio be about 15 to 20 times.

For coupling between hapten and carrier, various condensing agents can be used, but glutaraldehyde, carbodiimide, etc. are preferably used.

In immunizing mammals by means of bFGF or a protein complex, laboratory animals such as sheep, goats, rabbits, guinea pigs, rats and mice may be used, and rats and mice, especially mice, are preferred for obtaining monoclonal antibodies. As to the method of immunization, immunization is possible via any route such as subcutaneous, intraperitoneal, intravenous, intramuscular or intracutaneous injection, but it is preferable that the immunogen be injected mainly subcutaneously, intraperitoneally or intravenously (in particular, subcutaneously). In addition, immunizing interval, immunizing dose, etc. are also highly variable, allowing various methods to be carried out; the method in which immunization is conducted about 2 to 6 times at intervals of 2 weeks, and splenic cells taken out about 1 to 5 times, preferably about 2 to 4 days after the final immunization are used, for example, is commonly used. It is desirable that an immunizing dose of more than about 0.1 $\mu$g, preferably about 10 to 300 $\mu$g for each mouse, calculated on the peptide amount basis, be used in each injection. It is also desirable that a fusion experiment using a splenic cell be conducted after certification of increase in blood antibody titer by local blood sampling prior to excision of the spleen.

In the above-mentioned cell fusion of a splenic cell with a lymphoid cell, an excised mouse splenic cell, for example, is fused with an appropriate homogenic or heterogenic (preferably homogenic) lymphoid cell line having a marker such as hypoxanthine-guanine phosphoribosyltransferase deficiency (HGPRT$^-$) or thymidine kinase deficiency (TK$^-$). As the lymphoid cell line, myeloma cell is preferred, and the myeloma cell there is mentioned myeloma P3-X63-Ag. 8UI (Ichimori et al.: Journal of Immunological Methods, 80, 55 (1985)]. This fusion can be executed via e.g. the method developed by Köhler and Milstein [Nature, 256, 495 (1975)]. For example, myeloma cells and splenic cells, in an about 1:5 ratio, are suspended in a medium prepared by mixing together Iskov medium and Ham F-12 medium in a 1:1 ratio (hereinafter referred to as IH medium), and a fusing agent such as Sendai virus or polyethylene glycol (PEG) is used. Of course, dimethyl sulfoxide (DMSO) and/or other fusion promoters can also be added. The following are normally used: a degree of polymerization for the PEG of about 1000 to 6000, a treating time of about 0.5 to 30 minutes and a PEG concentration of about 10 to 80%. Efficient fusion can be achieved by about 4 to 10 minutes of PEG 6000 treatment at an about 35 to 55% concentration. The fused cells can be selectively grown using the hypoxanthine-aminopterin-thymidine medium [HAT medium; Nature, 256, 495 (1975)] or the like.

The culture supernatant of grown cells can be subjected to screening for the production of the desired antibody, and screening for antibody titer can be conducted as follows: In this case, the culture supernatant can first be assayed for the production of antibody to an immunized peptide by a method such as the radioimmunoassay (RIA) method or enzyme immunoassay (EIA) method. These methods are also widely modifiable. As an example of preferred method of assay, a method using EIA is described below. To a carrier such as cellulose beads the rabbit anti-mouse immunoglobulin antibody, for example, is beforehand coupled in accordance with a routine method, and the culture supernatant to be assayed and mouse serum are added thereto, and reaction is carried out at constant temperature (which means about 4° to 40° C.; this definition also applied hereinafter) for the specified time. After the reaction product is well washed, a peptide labeled with enzyme (prepared by coupling of an enzyme and a peptide in accordance with a routine method, followed by purification) is added, and reaction is carried out at constant temperature for the specified time. After the reaction product is well washed, an enzyme substrate is added, and reaction is carried out at constant temperature for the specified time, whereafter the resulting chromogenic substance can be assayed by absorptiometry or fluorometry.

It is desirable that the cells, which showed proliferation in the selective medium and secreted antibodies which combined with peptide used for the immunization, were subjected to cloning by limiting dilution analysis etc. The supernatant of the cloned cells is subjected to screening in the same manner as above to increase cells in the cells high in antibody titer, whereby monoclonal antibody producing hybridoma clones showing reactivity to the immunized peptide are obtained.

The hybridoma thus cloned is grown in liquid medium, for example, a medium prepared by adding about 0.1 to 40% bovine serum to RPMI-1640 [Moore, G. E. et al.; Journal of American Medical Association, 199, 549 (1967)]. Specifically, said monoclonal antibody can be obtained from the medium cultured for about 2 to 10 days, preferably about 3 to 5 days. The antibody can also be obtained from ascites fluids of mice which are intraperitoneally inoculated the hybridoma. For this purpose, in the case of mice, for example, about $1 \times 10^4$ to $1 \times 10^7$, preferably about $5 \times 10^5$ to $2 \times 10^6$ hybridoma cells are intraperitoneally inoculated to a mouse of BALB/c or similar strain, previously inoculated with mineral oil etc., and about 7 to 20 days later, preferably about 10 to 14 days later ascites fluid is collected. The antibody produced and accumulated in the ascites is subjected to, for example, ammonium sulfate fractionation and DEAE-cellulose column chromatography, whereby the desired monoclonal antibody can easily be isolated as a pure immunoglobulin.

A monoclonal antibody which combines specifically with bFGF is thus obtained.

The monoclonal antibody of the present invention combines specifically with the immunogen peptide bFGF. The monoclonal antibody of the present invention may also combine with a bFGF other than the immunogen peptide. The monoclonal antibody of the present invention is a monoclonal antibody to the immunogen peptide bFGF or its mutein. As the present monoclonal antibody reacts with only bFGF (and its mutein), the present monoclonal antibody combines specifically with bFGF.

As shown in Example 3 below, when human bFGF is used as an immunogen, a monoclonal antibody belonging to the immunoglobulin class IgM is obtained in some cases.

Since combining specifically with bFGF, the monoclonal antibody of the present invention is very useful as a reagent for bFGF assay. It also facilitates bFGF assay in living organs and tissues, so it is very useful also in obtaining basic information about bFGF (e.g., distribution in vivo). In the detection procedure on the bFGF in living organs and tissues, the measuring by EIA method or fluorescent antibody technique are generally employed. In order to measure the amount in the living organs and tissues, it is always employed Western blotting method on protein. In this method, a crude extract or partial purified sample of the extract is subjected to electrophoresis with acylamide gel, transferring to membrane filter, and then detection with HRP-anti bFGF antibody.

In addition, it is thought that some cancer cells produce bFGF by themselves to continue their proliferation on the basis of the bFGF. When anti-bFGF antibody is allowed to act on such cancer, the proliferation-promoting bFGF is neutralized, and the antibody is expected to exhibit cancer cell proliferation inhibition, that is, to act as an anticancer substance. In addition, the antibody can be used to determine the bFGF in bFGF-producing cancer, so it can also be applied to cancer diagnostic reagents. Moreover, based on the avidity of the said antibody to bFGF, an antibody affinity column can be prepared to use the antibody as a reagent for bFGF purification.

As the EIA method and RIA method for detecting or measuring bFGF, there are mentioned the following procedure.

For example, a purified antibody is fixed on 96 wells plastic plate (e.g. Immunoplate, Nunc, Denmark) at about 0.1 to 10 $\mu$g/well, glass beads, plastic beads. The fixation is carried out at about 4° C. for overnight, or at room temperature for about 0.4 to 4 hours, in case of plastic. In case of glass beads, the fixation is carried out in accordance with the method described in Proc. Natl. Acad. Sci. U.S.A., 80, 3513–3516 (1983). Thus obtained plate or beads to which the antibody has been fixed is subjected to adsorption reaction with the antigen bFGF (or its mutein). The adsorption reaction is generally carried out at room temperature for about 0.2 to 2 hours, preferably about 4° C. overnight. After the antigen-antibody reaction, adsorption reaction is carried out by adding an antibody which has been labeled with an enzyme in case of EIA or labeled with a radioisotope in case of RIA. As the enzyme to label an antibody, there are exemplified by horse radish peroxidase (HRP), alkaline phosphatase. As the examples of radioisotope labeling, there are mentioned $^{125}$I.

In case of EIA, a substrate such as 2,2'-adino-di[3-ethylbenzothiazoline sulfonate (6)] is employed for coloring when HRP is employed as a labeling enzyme.

In case of RIA, the radioactivity is measured by scintillation counter. The measuring the bFGF is carried out by comparing the absorbancy or radioactivity with those of the known amount of bFGF.

As the EIA method, there are mentioned sandwich EIA method, competitive EIA method, indirect EIA method. In the sandwich method, two antibodies are bound by mediating the antigen, bFGF. In the competitive EIA method, an antibody is fixed to a carrier, antigen bFGF which has been combined with a labeling enzyme or radioisotope, and a sample, so as to react competitively, and then measuring the amount of labeled antigen. In this competitive EIA method, the reaction conditions, and measuring the amount of bound antibody to antigen are the same as the sandwich EIA method. As the indirect EIA method, a sample and an antibody (which is not fixed) are reacted with each other, the unbound antibody is measured by a plate to which the antigen is fixed and an anti-mouse antibody. In this indirect EIA method, the reaction conditions and measuring method are those as mentioned above.

For the purpose of bFGF purification, efficient purification can be achieved by, for example, the method in which the purified relevant antibody, after coupling with an appropriate carrier such as the activated agarose bead in accordance with a routine method, is packed in a column, the crude sample containing bFGF such as culture supernatant or disrupted bacterial cells is adsorbed to the antibody affinity column, and the column is washed, whereafter bFGF is eluted with a chaotropic reagent such as KSCN (potassium thiocyanate) or under such slightly acidic conditions that bFGF is never inactivated.

The preparation of antibody column is carried out by coupling the monoclonal antibody of the present invention, purified from, for example, ascites fluid inoculated with hybridoma, with an appropriate carrier, by the method as follows:

Any carrier can be used, as long as it ensures the efficient adsorption specifically of bFGF after coupling, and enables the appropriate elution of bFGF after the adsorption; as the carrier there are mentioned polymer of agarose, cellulose or acrylamide, and as the carrier, for example, polyacrylamide gel beads activated so that primary amino group in protein is easily combined with, such as Affi-Gel-10 is used as appropriate in the manner as described below. The reaction between Affi-Gel-10 and antibodies is carried out in a buffer such as a solution of about 0.001 to 1M, preferably about 0.1M bicarbonate. As to reaction conditions, the reaction can be carried out at about 0° to 20° C. for about 10 to 24 hours at any pH level, but about 4° C., about 4 hours, and pH about 3 to 10 is preferably used for reaction conditions. Since more antibodies are adsorbed as the amount of antibodies per 1 m of Affi-Gel-10 increases, as long as the amount is less than about 50 mg; therefore, any quantitative ratio between Affi-Gel-10 and antibodies to be mixed together can be chosen within this range, but about 10 to 30 mg of antibodies is used as appropriate, considering binding efficiency and purifying efficiency in affinity column chromatography. These antibody-carrier conjugates can be used for an antibody colum by packing in an appropriate column after blocking the remaining unreacted active groups by a method such as the method in which the conjugates, after being well washed with the buffer used for the reaction, are kept standing several days, or the method in which a final concentration of about 0.05 to 0.1M of a compound having a primary amino group such as ethanolamine hydrochloric acid or glycine is added and reaction is carried out at about 4° C. for about 1 to 4 hours, or about 1 to 5% of protein such as bovine serum albumin (BSA) is added and reaction is carried out at 4° C. overnight.

In purification using the above-mentioned antibody column, for example a sample containing bFGF is dissolved in a buffer such as a phosphate buffer or a Tris hydrochloric acid and is adsorbed to the antibody column. Thereafter, the column is washed with the same buffer, and bFGF is then eluted. As eluents, there can be used slightly acidic solutions such as acetic acid solutions, solutions containing polyethylene glycol, solutions containing peptide which is more likely to combine with antibodies than the sample, high concentration salt solutions, and solutions prepared by combining these, and those which do not considerably accelerate the decomposition of bFGF are preferred.

The column effluent is neutralized with a buffer by a routine method. Where necessary, a purifying procedure using the above antibody column can be again carried out.

In this way, substantially pure bFGF mutein protein can be obtained. The substantially pure bFGF mutated protein according to this invention includes products whose bFGF mutated protein content is not less than 90% (w/w) and, more preferably, products whose bFGF mutein content is not less than 95% (w/w).

The bFGF solution thus obtained are subjected to dialysis, and, if necessary, can be made into a powder by lyophilization. In the lyophilization, there may be added stabilizers such as sorbitol, mannitol, dextrose, maltose and glycerol.

The hbFGF thus obtained possesses growth promoting activity of fibroblast cells and endothelial cells and angiogenic activity, and its toxicity is low; therefore, the hbFGF can be used as a cure promoter for burns, wounds, postoperative tissues, etc., or as a therapeutic agent for thrombosis, arteriosclerosis, etc. which is based on its neovascularizing effect. Furthermore, it can be used as a reagent for promoting cell cultivation.

For its pharmaceutical use, the hbFGF can be safely administered to warm-blooded mammals (e.g. humans, mice, rats, hamsters, rabbits, dogs, cats) parenterally or orally either per se in a powder form or in the form of pharmaceutical compositions (e.g., injection, tablet, capsule, solution, ointment) made up together with pharmacologically acceptable carriers, excipients and/or diluents.

Injectable preparations can be produced by a conventional method using, for example, physiological saline or an aqueous solution containing glucose and/or other adjuvant or adjuvants. Tablets, capsules and other pharmaceutical compositions can also be prepared in accordance with a conventional method. When prepared for use as a pharmaceutical, care should be taken that aseptic conditions are used and that the resultant product is sterile, low in pyrogens and endotoxins.

When used for the above pharmaceutical purposes, the hbFGF is administered, for example, to the above warm-blooded mammals in an appropriate amount selected from the range of from about 1 ng to 100 $\mu$g/kg body weight a day according to the route of administration, symptoms, etc.

When used as a reagent for promoting cell cultivation, the hbFGF is added to the medium preferably in an amount of 0.01 to 10 $\mu$g, more preferably 0.1 to 10 $\mu$g per liter of medium.

The mutein of hbFGF can also be used as with the above hbFGF.

Thus, since combining specifically with bFGF, the monoclonal antibodies of the present invention can be advantageously used for bFGF assay reagents and for purifying bFGF.

In addition, of the monoclonal antibodies of the present invention, those which are high in antibody valency are advantageous in that, when they are used as bFGF assay reagents, the amount of other reagents prepared at the time of use, for example, antiserum, is saved. Furthermore, bFGF purification to higher degree can be achieved by the use thereof.

In the specification and drawings of the present invention, the abbreviations used for bases, amino acids and so on are those recommended by the IUPAC-IUB Commission on Biochemical Nomenclature or those conventionally used in the art. Examples thereof are given below. Amino acids for which optical isomerism is possible are, unless otherwise specified, in the L form.

DNA: Deoxyribonucleic acid
cDNA: Complementary deoxyribonucleic acid
A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate Tdr: Thymidine
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine In Reference Examples mentioned below, the human bFGF constituent amino acids shall be numbered according to the rule, in which Met added to the N-terminal of the peptide having Thr for X and Ser for Y in the above-mentioned amino acid sequence (II), said Met is numbered as the first.

BRIEF DESCRIPTION OF THE DRAWINGS

FIG. 1 shows the human bFGF-encoding base sequence as determined in Reference Example 1 and the amino acid sequence deducible from said base sequence.

Figure 2:
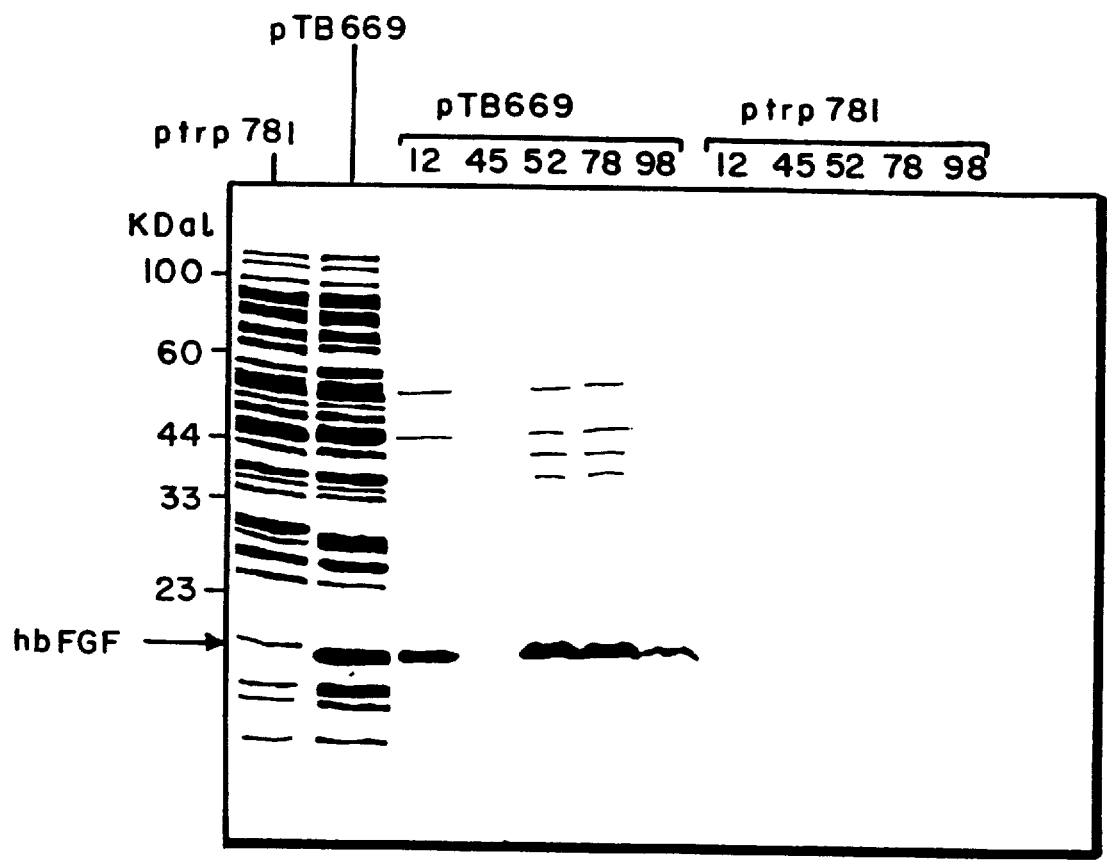
FIG. 2 shows the polyacrylamide gel electrophoresis patterns on immunoprecipitation as obtained in Example 5.

The mouse HbF99 cell, mouse HbF161 cell and mouse HbF165 cell obtained in Example 2 (3) to be described later have been deposited at Institute for Fermentation, Osaka (IFO), Japan since Jan. 28, 1987 respectively under the following accession numbers:

Mouse HbF99 cell: IFO 50122

Mouse HbF161 cell: IFO 50123

Mouse HbF165 cell: IFO 50124

The mouse hybridomas HbF12, HbF52, HbF78, and HbF98 obtained in Example 4 to be described later have respectively been deposited at the IFO since Aug. 17, 1987 under the following accession numbers:

Mouse HbF12 cell: IFO 50142

Mouse HbF52 cell: IFO 50143

Mouse HbF78 cell: IFO 50144

Mouse HbF98 cell: IFO 50145

The following transformants which were produced in the Reference Examples mentioned below were deposited at IFO and at the Fermentation Research Institute, Agency of Industrial Science and Technology, Ministry of International Trade and Industry (FRI), Japan under the accession numbers on the deposit dates shown in Table 1 (The deposit dates are indicated in parentheses.). As to the deposit number of FRI, FERM BP number denotes the number of deposit under the Budapest Treaty; and in case both FERM P number and FERM BP number are described, it shows that the deposit under the number of FERM P has been converted to the deposit under Budapest Treaty and the transformants have been stored at FRI under the number of FERM BP.

TABLE 1

| Transformants | IFO | FRI | |
|---|---|---|---|
| E. coli K12 DHI/pTB 627 [Reference Example 1] | IFO 14494 (March 13, 1986) | FERM P-8726 (April 2, 1986) | FERM BP-1280 |
| E. coli K12 MM294/pTB 669 [Reference Example 2] | IFO 14532 (August 11, 1986) | FERM P-8918 (August 21, 1986) | FERM BP-1281 |
| E. coli DH1/ pTB 739 [Reference Example 5] | IFO 14575 (February 18, 1987) | FERM P-9216 (February 25, 1987) | FERM BP-1641 |
| E. coli DH1/ pTB 742 [Reference Example 6] | IFO 14584 (March 24, 1987) | FERM P-9307 (March 30, 1987) | FERM BP-1642 |
| E. coli DH1/ pTB 743 [Reference Example 7] | IFO 14585 (March 24, 1987) | FERM P-9308 (March 30, 1987) | FERM BP-1643 |
| E. coli DH1/ pTB 744 [Reference Example 8] | IFO 14586 (March 24, 1987) | FERM P-9309 (March 30, 1987) | FERM BP-1644 |
| E. coli MM294/pTB 762 [Reference Example 10] | IFO 14613 (May 27, 1987) | FERM P-9409 (June 11, 1987) | FERM BP-1645 |
| E. coli MM294/pTB 795 [Reference Example 12] | IFO 14700 (January 14, 1988) | | FERM BP-1660 (January 20, 1988) |

TABLE 1-continued

| Transformants | IFO | FRI |
|---|---|---|
| E. coli MM294/pTB 796 [Reference Example 13] | IFO 14701 (January 14, 1988) | FERM BP-1661 (January 20, 1988) |
| E. coli MM294/pTB 797 [Reference Example 14] | IFO 14702 (January 14, 1988) | FERM BP-1662 (January 20, 1988) |

EXAMPLES

The present invention will now be illustrated in more detail by means of the following working examples, but the present invention is never limited thereby.

Reference Example 1

(Construction of a plasmid containing an hbFGF-encoding gene)

(1) Isolation of cDNA-containing plasmid:

A cDNA library with *Escherichia coli* x1776 as the host as produced by inserting cDNA synthesized from human foreskin derived primary culture cell mRNA into the pCD vector [Okayama et al.: Molecular and Cellular Biology, 3, 280 (1983)] was provided by Dr. Okayama at the National Institute of Child Health and Human Development, Bethesda, U.S.A. The plasmid DNA was extracted from this cDNA library by the alkaline extraction method [Birnboim, H. C. and Doly, J.: Nucleic Acids Research, 1, 1513 (1979)] and *Escherichia coli* DH1 was infected with this DNA. A cDNA library comprising about $2 \times 10^6$ clones was thus produced with *Escherichia coli* DH1 as the host.

The above cDNA library with *Escherichia coli* DH1 used therein was plated on 10 pieces of nitrocellulose filter (Millipore's HATF filter) in an amount of about $5 \times 10^4$ clones per filter. Using these filters as master filters, 20 replica filters were prepared in 10 pairs corresponding to the master filters. *Escherichia coli* cells on these replica filters were lysed with a 0.5N NaOH solution and plasmid DNAs exposed and denatured were immobilized on the filters [Grunstein, M. & Hogness, D. S.: Proc. Natl. Acad. Sci. U.S.A., 72, 3961(1975)].

Based on the amino acid sequence of bovine basic fibroblast growth factor as reported by F. Esch et al. [Proc. Natl. Acad. Sci. U.S.A., 82, 6507 (1985)], base sequences corresponding to two amino acid sequences covering amino acid Nos. 13–20 (Pro-Pro-Gly-His-Phe-Lys-Asp-Pro) and amino acid Nos. 89–96 (Thr-Asp-Glu-Cys-Phe-Phe-Phe-Glu), respectively were chemically synthesized. (In some codons, the third letter was selected arbitrarily. Thus, the base sequences synthesized were 5' $GG^A/_G$ $TC^T/_C$ $TT^A/_G$ $AA^A/G$ TG$\underline{G}$CC$\underline{A}$GG$\underline{A}$GG and 5' $TC^A/_G$ $AA^A/_G$ $AA^A/_G$ $AA^A/_G$ $CA^T/_C$ TC$\underline{G}$TC$\underline{G}$GT, with each underlined base being the one selected.) These oligonucleotides were labeled with $^{32}P$ at the 5' end by treating said oligonucleotides in 50 μl of reaction mixture [0.1 μg of oligonucleotide, 50 mM Tris-HCl, pH 8.0, 10 mM MgCl$_2$, 10 mM mercaptoethanol, 50 μCi γ-$^{32}P$ ATP (>5,000 Ci/mmole), 3 units of T4 polynucleotide kinase (Takara Shuzo, Japan)] at 37° C. for 1 hour.

The thus-labeled oligonucleotides of the above two kinds were individually hybridized as probes with the replica filters. The hybridization reaction was conducted in 10 ml of a 100 μg/ml denatured salmon sperm DNA solution containing 10 μCi of probe in 5×SSPE [180 mM NaCl, 10 mM NaH$_2$PO$_4$, 1 mM EDTA (pH 7.4)] and 5×Denhardt's with 0.1% SDS at 35° C. for 16 hours. After reaction, the filters were washed with a 0.1% SDS solution in 5×SSC [0.15M NaCl, 0.015M sodium citrate] three times each at room temperature for 30 minutes and then two times each at 45° C. for 30 minutes [T. Maniatis et al.: "Molecular Cloning", Cold Spring Harbor Laboratory, p. 309 (1982)].

Radioautograms were taken for the washed filters. A bacterial strain capable of reacting with the both kinds of probe was searched for by superposing the radioautograms for each pair of replica filters. In this manner, a strain [*Escherichia coli* K12 DH1/pTB627 (IFO 14494, FERM BP-1280)] capable of reacting with the two kinds of probe was obtained from among $5 \times 10^5$ colonies.

(2) The plasmid DNA (pTB627) was extracted from the strain obtained above in (1) [*Escherichia coli* K12 DH1/pTB627 (IFO 14494, FERM BP-1280)] by the alkaline extraction method [Nucleic Acids Research, 1, 1513 (1979)] and purified.

(3) Then, the base sequence of the cDNA portion encoding hbFGF was determined by the dideoxynucleotide synthetic chain termination method [J. Messing et al.: Nucleic Acids Research, 9, 309 (1981)]. The amino acid sequence deduced from said base sequence is shown in FIG. 1.

Reference Example 2

(Expression of hbFGF-encoding gene in *Escherichia coli*)

Construction of hbFGF expression plasmid pTB669:

The plasmid pTB627 obtained in Reference Example 1 (2) mentioned above and containing the hbFGF cDNA was cleaved with the restriction enzymes AvaI and BalI, whereby a 0.44 kb DNA fragment containing the hbFGF-encoding region was obtained. A BglII linker, pCAGATCTG, was ligated with this DNA fragment at its BalI cleavage site (blunt end) by T4 DNA ligase, and a 0.44 Kb AvaI-BglII DNA fragment was isolated. T4 DNA ligase was allowed to act on this 0.44 Kb AvaI-BglII fragment to thereby cause ligation between the BglII cleavage sites. Then, DNA polymerase (Klenow fragment) reaction was carried out in the presence of dXTPs to render the AvaI cleavage sites blunt. This DNA fragment was ligated with phosphorylated synthetic oligonucleotides, 5'AATTCTATGCCAGCATTGC3' and 5'GCAATGCTGGCATAG3', in the presence of T4 DNA ligase. An about 0.46 kb DNA fragment was then prepared by cleavage with EcoRI-BglII. Separately, the trp promoter-containing plasmid ptrp781 [Kurokawa, T. et al.: Nucleic Acids Research, 11, 3077–3085 (1983)] was cleaved with PstI and rendered blunt-ended by T4 DNA polymerase reaction. The BglII linker pCAGATCTG was joined to the above cleavage product at the blunt ends thereof by T4 DNA ligase reaction; then the ligation product was cleaved with EcoRI-BglII and an about 3.2 kb DNA fragment containing the trp promoter, the tetracycline resistance gene and the plasmid replication origin was isolated. This 3.2 kb DNA fragment was ligated with the above-mentioned 0.46 kb EcoRI-BglII DNA fragment containing the hbFGF-encoding gene region by T4 DNA ligase reaction, whereby an hbFGF expression plasmid, pTB669, was constructed.

This plasmid pTB669 was used to transform *Escherichia coli* DH1 to give a transformant carrying the plasmid pTB669, namely *Escherichia coli* DH1/pTB669.

pTB669 was also used in the same manner to transform the *Escherichia coli* strains K12MM294 and C600 to give *Escherichia coli* K12 MM294/pTB669 (IFO 14532, FERM BP-1281) and *E. coli* C600/pTB669, respectively.

Reference Example 3

(Purification of human basic fibroblast growth factor (hbFGF))

*Escherichia coli* K12MM294/pTB669 (IFO 14532, FERM BP-1281) as obtained in Reference Example 2 was cultivated in M9 medium [Maniatis, T. et al.: Molecular Cloning (1982), A Laboratory Manual, Cold Spring Harbor Laboratory, U.S.A.] containing 1% glucose, 0.4% casamino acid and 8 μg/ml tetracycline. When the Klett value reached about 200, 3-β-indolylacrylic acid was added to 25 μg/ml, and the cultivation was continued for 4 more hours. Thereafter, cells were harvested and suspended in one twentieth volume of 10% sucrose solution in 20 mM Tris-HCl, pH 7.6. To this suspension were added phenylmethylsulfonyl fluoride (PMSF) to 1 mM (final concentration), EDTA to 10 mM, NaCl to 0.1M, spermidine hydrochloride to 10 mM and lysozyme to 100 μg/ml. After allowing to stand at 0° C. for 45 minutes, the whole mixture was sonicated for 30 seconds. The sonication product was centrifuged at 18,000 rpm (Sorvall centrifuge, SS 34 rotor, U.S.A.) for 30 minutes to give a supernatant, which was used as the cell extract.

A 25-ml portion of this extract (as prepared from 500 ml of culture broth) was passed through a DEAE-cellulose (DE52, Whatman, England) column (diameter 2×10 cm) equilibrated with 0.2M NaCl solution in 20 mM Tris-HCl, pH 7.6 to thereby remove nucleic acid components in the extract. The effluent from the column and the column washings resultant from washing with 0.2M NaCl solution in 20 mM Tris-HCl, pH 7.6 were collected and combined (DEAE effluent fraction 44 ml).

A 14-ml portion of this fraction was applied to a high performance liquid chromatograph (Gilson, France) equipped with a heparin column Shodex AF-pak HR-894 (8 mm ID×5 cm, Showa Denko, Japan). The column was washed with 20 mM Tris-HCl, pH 7.6. Thereafter, elution was performed on a linear gradient of 0.5–2M NaCl in 20 mM Tris-HCl buffer, pH 7.6, (eluent volume 60 ml, flow rate 1.0 ml/min).

The hbFGF eluted by this procedure showed a single band in SDS-polyacrylamide gel electrophoresis, and it was thus found to be sufficiently purified and suitable for use as an antigen. The assay of hbFGF was conducted using the following conditions.

A Nunc 96-well microtiter plate (flat bottomed) was sown with mouse BALB/c3T3 cells (2×10$^3$ cells per well) with DMEM medium containing 5% calf serum (0.2 ml per well) and the cells were cultured. Next day, the medium was replaced with DMEM medium containing 0.5% calf serum. After 3 days of cultivation, dilutions of the cell extract as prepared by serial 5-fold dilution with DME medium containing 0.5% BSA were added in an amount of 10 μl per well. After 20 hours of continued cultivation, 2 μl of $^3$H-Tdr (5 Ci/mmol, 0.5 mCi/ml RCC Amersham) was added to each well. Six hours later, cells in each well were scraped off by treatment with phosphate buffer (PBS) containing 0.2% trypsin and 0.02% EDTA and collected on a glass filter using a Titertek cell harvester, and the quantity of $^3$H-Tdr taken up by the cells was measured using a scintillation counter.

Reference Example 4

(Production of recombinant DNA having mutein-encoding base sequence)

(1) Cloning of human bFGF gene M13 vector

The plasmid pTB669 obtained in Reference Example 2 was digested with the restriction enzymes EcoRI and BamHI. Phage vector M13mp8 [J. Messing: Methods in Enzymology, 101, 20–78 (1983)] replicative form (RF) DNA was digested with the restriction enzymes EcoRI and BamHI. The DNA fragment thus obtained was mixed with the human bFGF DNA fragment derived from the pTB669 which was previously digested with EcoRI and BamHI. The mixture was then ligated together by T4 DNA ligase. The ligated DNA was transformed into infectable cells of *Escherichia coli* JM105 strain, and the cells were sown on a plate containing Xga1 as the indicator species [J. Messing et al.: Nucleic Acids Research, 9, 309–321 (1981)]. The plaque containing the recombinant phage (white plaque) was picked up, and the base sequence of the recombinated segment was determined by the dideoxynucleotide synthetic chain termination method [J. Messing et al.: Nucleic Acids Research, 9, 309 (1981)], whereby it was confirmed that human bFGF DNA was accurately inserted.

From this M13PO clone was purified single-stranded phage DNA, which was used as a template for site-directed mutagenesis using synthetic oligonucleotide.

(2) Site-specific mutagenesis

Forty picomoles of the synthetic oligonucleotide:

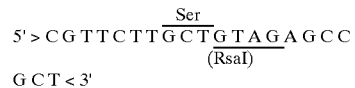

[the primer for converting Cys 26 to Ser (the recognition sequence for restriction enzyme Rsa I disappears)] was treated with 9 units of T4 kinase at 37° C. for 1 hour in 50 μl of a solution containing 0.1 mM adenosine triphosphate (ATP), 50 mM hydroxymethylaminomethane hydrochloride (Tris-HCl), pH 8.0, 10 mM MgCl$_2$ and 5 mM dithiothreitol (DTT). This kinase-treated primer (12 picomoles) was heated at 67° C. for 5 minutes and then at 42° C. for 25 minutes in 50 μl of a mixture containing 50 mM NaCl, 1.0 mM Tris-HCl, pH 8.0, 10 mM MgCl$_2$ and 10 mM β-mercaptoethanol, whereby the primer was hybridized to 5 μg of single-stranded (ss) M13-PO DNA. After annealing, the mixture was cooled on ice, and was added to 50 μl of a reaction mixture containing 0.5 mM dideoxynucleotide triphosphate (dNTP), 80 mM Tris-HCl, pH 7.4, 8 mM MgCl$_2$, 100 mM NaCl, 9 units of DNA polymerase I Klenow fragment, 0.5 mM ATP and 2 units of T4 DNA ligase, and reaction was carried out at 37° C. for 3 hours and 25° C. for 2 hours. The reaction was terminated by adding 2 μl of 0.2 mM EDTA. The reaction product was used to transform infectable JM 105 cells, and the cells were grown overnight. Thereafter, ssDNA was isolated from the medium's supernatant. Using this ssDNA as the template for the second cycle of primer elongation, gel-purified RF DNA was transformed into infectable JM 105 cells. The cells were sown over an agar plate and cultivated overnight, whereby a phage plaque was obtained.

(3) Site-directed mutagenesis

The procedure of the above term (2) was repeated, but the synthetic oligonucleotide primer used was

which converts cysteine 70 to serine (A recognition sequence for restriction enzyme HaeII is produced).

(4) Site-directed mutagenesis

The procedure of the above term (2) was repeated, but the synthetic oligonucleotide primer used was

which converts cysteine 88 to serine (A recognition sequence for restriction enzyme AluI is produced).

(5) Site-directed mutagenesis

The procedure of the above term (2) was repeated, but the oligonucleotide primer used was

which converts cysteine 93 to serine (A recognition sequence for restriction enzyme HinfI is produced).

(6) Screening and identification of mutated plaques

Plates containing mutated M13-PO plaques [above term (1)] and two plates containing unmutated M13-PO phage plaques were cooled to 4° C., and the plaques from each plate were transferred to two round nitrocellulose filters by superposing a dry filter on the agar plate for 5 minutes in the case of the first filter, or by superposing a dry filter for 15 minutes in the case of the second filter. Then, the filters were placed on a thick filter paper and immersed in a solution containing 0.2N NaOH, 1.5M NaCl and 0.2% Triton X-100, and then on a filter paper in a solution containing 0.5M Tris-HCl, pH 7.5 and 1.5M NaCl for 5 more minutes, to thereby neutralize the filters. The filters were washed on a filter by immersing them twice in 2×SSC (standard sodium citrate). The filters were then allowed to dry in air, after which they were dried at 80° C. in a vacuum oven for 2 hours. The duplicated filters were subjected to prehybridization at 55° C. for 4 hours in 10 ml/filter DNA hybridization buffer (5×SSC), pH 7.0/4×Denhardt's solution (polyvinylpyrrolidone, Ficoll, and bovine serum albumin, 1×=0.02% for each)/0.1% sodium dodecylsulfate (SDS)/50 mM sodium phosphate buffer, pH 7.0/100 μg/ml denatured salmon sperm DNA. The oligonucleotide primer was hybridized to $10^5$ cpm/ml at 42° C. for 24 hours. The filters were washed in washing buffers containing 0.1% SDS and decreasing amounts of SSC at 50° C. for 30 minutes for each wash. That is, the filters were washed first with the buffer containing 2×SSC, and the control filters containing unmutated M13-PO plaques were examined for radioactivity by means of a Geiger counter. While reducing SSC concentration step by step, the filters were washed until no detectable radioactivity remained on the control filters containing unmutated M13-PO plaques. The minimum SSC concentration used was 0.1×SSC. The filters were air-dried and exposed to film at −70° C. for 2 to 3 days to thereby take radioautograms. A total of 10,000 mutated M13-PO plaques and 100 unmutated control plaques were screened by means of the kinase-treated oligonucleotide probe. None of the control plaques hybridized to the probe, while 3 to 10 of the mutated M13-PO plaques hybridized to the probe.

One of the mutated M13-O plaques was picked up and inoculated to JM105 medium. From the supernatant was prepared ssDNA, and from the cell pellet was prepared double-stranded (ds) DNA. Using appropriate oligonucleotide primers and ssDNAs, the base sequences were analyzed.

As a result, it was respectively confirmed that TGC (Cys26) codon had been converted to TCT (Ser) codon, TGT (Cys7O) codon had been converted to AGC (Ser) codon, TGT (Cys88) codon had been converted to TCT (Ser) codon, and TGT (Cys93) codon had been converted to TCT (Ser) codon.

Of the mutated M13-PO phages, the phage in which the codon Cys-26 had been converted to Ser was designated M13-P1; the phage in which the codon Cys-70 had been Ser, M13-P2; the phage in which the codon Cys-88 had been converted to Ser, M13-P3; and the phage in which the codon Cys-93 had been converted to Ser, M13-P4.

Reference Example 5

(Expression of human bFGF mutein-encoding gene in *Escherichia coli* )

(1) Construction of human bFGF mutein expression plasmid pTB739)

The M13-P1 replicative form (RF) obtained above in Reference Example 4 was cleaved with the restriction enzymes EcoRI and PstI to thereby obtain an about 0.5 kb DNA fragment including the human bFGF mutein-encoding region.

Separately, the trp promoter-containing plasmid ptrp781 [Kurokawa, T. et al.: Nucleic Acids Res., 11, 3077–3085 (1983)] was cleaved with EcoRI-PstI, and an about 3.2 kb DNA fragment containing the trp promoter, the tetracycline resistance gene and the plasmid replication origin was isolated. This 3.2 kb DNA fragment was ligated with the above-mentioned 0.5 kb EcoRI-PstI DNA fragment containing the human bFGF mutein-encoding gene region by T4 DNA ligase reaction, whereby a human bFGF mutein expression plasmid, pTB739, was constructed.

This plasmid pTB739 was used to transform *Escherichia coli* DH1 to give a transformant carrying the plasmid pTB739 containing the mutein-encoding gene, namely *Escherichia coli* DH1/pTB739 (IFO 14575, FERM BP-1641).

(2) Preparation of cell extract

The above transformant was cultivated in M9 medium containing 1% glucose, 0.4% casamino acid and 8 μg/ml tetracycline. When the Klett value was about 200, 3-β-indolylacrylic acid was added to 25 μg/ml, and the cultivation was continued for 4 more hours. Thereafter, cells were harvested and suspended in one twentieth volume of 10% sucrose solution in 20 mM Tris-HCl, pH 7.6. To this suspension were added phenylmethylsulfonyl fluoride (PMSF) to 1 mM (final concentration), EDTA to 10 mM, NaCl to 0.1M, spermidine hydrochloride to 10 mM and lysozyme to 100 μg/ml. After allowing to stand at 0° C. for 45 minutes, the whole mixture was sonicated for 30 seconds. The sonication product was centrifuged at 18,000 rpm (Sorvall centrifuge, SS 34 rotor, U.S.A.) for 30 minutes to give a supernatant, which was used as the cell extract.

(3) Human bFGF activity of cell extract

A Nunc 96-well microtiter plate (flat bottomed) was sown with mouse BALB/c3T3 cells ($2 \times 10^3$ cells per well) with DMEM medium containing 5% calf serum (0.2 ml per well) and the cells were cultured. Next day, the medium was replaced with DMEM medium containing 0.5% calf serum. After 3 days of cultivation, dilutions of the cell extract as prepared by serial 5-fold dilution with DME medium containing 0.5% BSA were added in an amount of 10 μl per well. After 20 hours of continued cultivation, 2 μl of $^3$H-Tdr (5 Ci/mmol, 0.5 mCi/ml RCC Amersham) was added to each well. Six hours later, cells in each well were scraped off by treatment with phosphate buffer (PBS) containing 0.2% trypsin and 0.02% EDTA and collected on a glass filter using a Titertek cell harvester, and the quantity of $^3$H-Tdr taken up by the cells was measured using a scintillation counter.

The cell extract of *E. coli* DH1/pTB739 thereby tested showed FGF activity.

The mutein CS1 in which the 26-position Cys of human bFGF had been replaced by Ser was thus obtained.

Reference Example 6

(Expression in *Escherichia coli* of gene encoding human bFGF mutein)
(1) Construction of the plasmid pTB742 for human bFGF mutein expression The M13-P2 replicative form (RF) obtained in Reference Example 4 above was cleaved using the restriction enzymes EcoRI and PstI to obtain an about 0.5 kb DNA fragment containing a region which encodes a human bFGF mutein.

Separately, a plasmid ptrp781 DNA containing a trp promoter was cleaved using EcoRI-PstI to separate an about 3.2 kb DNA fragment containing a trp promoter, a tetracycline resistance gene and a plasmid replication initiation site. This 3.2 kb DNA fragment and the above-mentioned 0.5 kb EcoRI-PstI DNA fragment containing a gene region encoding a human bFGF mutein were ligated together by T4 DNA ligase reaction to construct the plasmid pTB742 for the expression of a human bFGF mutein.

Using this plasmid pTB742, *Escherichia coli* DH1 was transformed, whereby the strain *Escherichia coli* DH1/pTB742 (IFO 14584, FERM BP-1642) was obtained, which harbors the plasmid pTB742 containing the mutein-encoding gene.
(2) Preparation of bacterial cell extract The above-mentioned transformant was cultured by the method described in Reference Example 5 (2) to give a supernatant, which was then used as a bacterial cell extract.
(3) Human bFGF activity of the bacterial cell extract A determination was made of the human bFGF activity on the bacterial cell extract obtained in (2) above, by the method described in Reference Example 5 (3).

The bacterial cell extract of *E. coli* DH1/pTB742 thereby tested exhibited FGF activity.

The mutein CS2, in which Cys at the 70-position of human bFGF had been replaced by Ser, was thus obtained.

Reference Example 7

(Expression in *Escherichia coli* of gene encoding human bFGF mutein)
(1) Construction of the plasmid pTB743 for human bFGF mutein expression The M13-P3 replicative form (RF) obtained in Reference Example 4 above was cleaved using the restriction enzymes EcoRI and PstI to obtain an about 0.5 kb DNA fragment containing a region which encodes a human bFGF mutein.

Separately, a plasmid ptrp781 DNA containing a trp promoter was cleaved using EcoRI-PstI to separate an about 3.2 kb DNA fragment containing a trp promoter, a tetracycline resistance gene and a plasmid replication initiation site. This 3.2 kb DNA fragment and the above-mentioned 0.5 kb EcoRI-PstI DNA fragment containing a gene region encoding a human bFGF mutein were ligated together by T4 DNA ligase reaction to construct the plasmid pTB743 for the expression of human bFGF mutein.

Using this plasmid pTB743, *Escherichia coli* DH1 was transformed, whereby the strain *Escherichia coli* DH1/pTB743 (IFO 14585, FERM BP-1643) was obtained, which harbors the plasmid pTB743 containing the mutein-encoding gene.
(2) Preparation of bacterial cell extract The above-mentioned transformant was cultured in the manner described in Reference Example 5 (2) to give a supernatant, which was then used as a bacterial cell extract.
(3) Human bFGF activity of the bacterial cell extract A determination was made of the human bFGF activity of the bacterial cell extract obtained in (2) above, by the method described in Reference Example 5 (3).

The bacterial cell extract of *E. coli* DH1/pTB743 thereby tested exhibited FGF activity.

The mutein CS3, in which Cys at the 88-position of human bFGF had been replaced by Ser, was thus obtained.

Reference Example 8

(Expression in *Escherichia coli* of gene which encodes human bFGF mutein)
(1) Construction of the plasmid pTB744 for human bFGF mutein expression The M13-P4 replicative form (RF) obtained in Reference Example 4 above was cleaved using the restriction enzymes EcoRI and PstI to obtain an about 0.5 kb DNA fragment containing a region which encodes a human bFGF mutein.

Separately, a plasmid ptrp781 DNA containing a trp promoter was cleaved using EcoRI-PstI to separate an about 3.2 kb DNA fragment containing a trp promoter, a tetracycline resistance gene and a plasmid replication initiation site. This 3.2 kb DNA fragment and the above-mentioned 0.5 kb EcoRI-PstI DNA fragment containing a gene region encoding a human bFGF mutein were ligated together by T4 DNA ligase reaction to construct the plasmid pTB744 for the expression of a human bFGF mutein.

Using this plasmid pTB744, *Escherichia coli* DH1 was transformed, whereby the strain *Escherichia coli* DH1/pTB744 (IFO 14586, FERM BP-1644) was obtained, which harbors the plasmid pTB744 containing the mutein-encoding gene.
(2) Preparation of bacterial cell extract The above-mentioned transformant was cultured by the method described in Reference Example 5 (2) to give a supernatant, which was then used as a bacterial cell extract.
(3) Human bFGF activity of the bacterial cell extract A determination was made of the human bFGF activity of the bacterial cell extract obtained in (2) above, by the method described in Reference Example 5 (3).

The bacterial cell extract from *E. coli* DH1/pTB744 thereby tested exhibited FGF activity.

The mutein CS4, in which Cys at the 93-position in human bFGF had been replaced by Ser was thus obtained.

Reference Example 9

(Screening and identification of plaques which were made mutagenic)

Plates containing mutated M13-P2 phage plaques obtained in Reference Example 4 and two plates containing unmutated M13-P2 phage plaques obtained in Reference Example 4 were cooled to 4° C., and the plaque from each plate was transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl (pH 7.5) and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 µg/ml denatured salmon sperm DNA. Hybridization was carried out at 42° C. for 24 hours with $10^5$ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2×SSC; the control filters, which contained unmutated M13-P2 plaques, were examined for radioactivity using a Geiger counter. While stepwise reducing SSC concentration, the control filters were washed until no detectable radioactivity remained on the filters. The minimum of the used SSC concentrations was 0.1×SSC. The filters were allowed to dry in air, and radioautographs were taken by 2 to 3 days of exposure at −70° C. Screening was carried out of 10,000 mutated M13-P2 plaques and 100 unmutated control plaques using a kinase-treated oligonucleotide probe. None of the control plaques hybridized to the probe, while 3 to 10 of the mutated M13-P2 plaques hybridized to the probe.

One of the mutated M13-P2 plaques was taken, and was inoculated to a JM105 culture medium. From the resulting supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the TGC (Cys-26) codon had been changed to a TCT (Ser) codon; the TGT (Cys-88) codon, to a TCT (Ser) codon; and the TGT (Cys-93) codon, to a TCT (Ser) codon.

Of the mutated M13-P2 phages, the phage in which the codons Cys-26 and -70° had become Ser-encoding codons was named M13-P12; the phage in which the codons Cys-70 and -88 had become Ser-encoding codons, M13-P23; and the phage in which the codons Cys-70 and -93 had become Ser-encoding codons, M13-P24.

Reference Example 10

(Expression in *Escherichia coli* of gene encoding human bFGF mutein)
(1) Construction of the plasmid pTB762 for human bFGF mutein expression The M13-P23 replicative form (RF) obtained in Reference Example 9 above was treated in the manner described in Reference Example 5 (1) to construct the plasmid pTB762 for human bFGF mutein expression.

Using this plasmid pTB762, *Escherichia coli* MM294 was transformed, whereby the strain *Escherichia coli* MM294/pTB762 (IFO 14613, FERM BP-1645) was obtained, which harbors the plasmid pTB762 containing the mutein-encoding gene.
(2) Preparation of bacterial cell extract The above-mentioned transformant was cultured by the method described in Reference Example 5 (2) to give a supernatant, which was then used as a bacterial cell extract.
(3) Human bFGF activity of the bacterial cell extract A determination was made of the human bFGF activity of the bacterial cell extract obtained in (2) above, by the method described in Reference Example 5 (3).

The bacterial cell extract from *E. coli* MM294/pTB762 thereby tested exhibited FGF activity.

The mutein CS23, in which Cys at the 70-position and at the 88-position had been replaced by Ser, was thus obtained.

Reference Example 11

(Production of recombinant DNAs having mutein-encoding base sequence)
(1) Cloning of M13 vector for human bFGF gene The plasmid pTB669 obtained in Reference example 2 was digested with the restriction enzymes EcoRI and BamHI. Phage vector M13mp8 [J. Messing, Methods in Enzymology, 101, 20–78 (1983)] replicative form (RF) DNA was mixed with a human bFGF DNA fragment derived from pTB669, previously digested with EcoRI and BamHI. The mixture was then subjected to ligation using T4 DNA ligase. The resulting ligated DNA was transformed into infectable cells of the strain *Escherichia coli* JM105; the transformant cells were spread over a plate whose indicator species was Xgal [J. Messing et al., Nucleic Acids Research, 9, 309–321 (1981)]; the plaque containing the recombinant phage (white plaque) was picked up; the base sequence of the recombinated region was determined by the dideoxynucleotide synthesis chain termination method [J. Messing et al., Nucleic Acids Research, 9, 309 (1981)], whereby it was confirmed that the human bFGF DNA had been accurately inserted.

From this M13-PO clone was purified a single-stranded phage DNA, which was used as a template for site-directed mutagenesis using a synthetic oligonucleotide.
(2) Site-specific mutagenesis In the presence of 0.1 mM adenosine triphosphate (ATP), 50 mM hydroxymethylaminomethane hydrochloride (Tris-HCl) having a pH-value of 8.0, 10 mM $MgCl_2$, 5 mM dithiothreitol (DTT) and 9 units of T4 kinase, in a total amount of 50 µl, 40 picomoles of the synthetic oligonucleotide:

5'-CGGGCATGAATTCGCCGCT-3'

[primer for producing in the base sequence a recognition site for the restriction enzyme EcoRI, and subsequently changing Pro-14 to Met] was treated with T4 kinase at 37° C. for 1 hour. This kinase-treated primer (12 picomoles) was heated at 67° C. for 5 minutes, and at 42° C. for 25 minutes, in 50 µl of a mixture containing 50 mM NaCl, 1.0 mM Tris-HCl having a pH-value of 8.0, 10 mM $MgCl_2$ and 10 mM β-mercaptoethanol, whereby it was hybridized to 5 µg of the single-stranded (ss) M13-PO DNA. The annealed mixture was then cooled on ice, and was added to 50 µl of a reaction mixture containing 0.5 mM deoxynucleotide triphosphate (dNTP), 80 mM Tris-HCl having a pH-value of 7.4, 8 mM $MgCl_2$, 100 mM NaCl, 9 units of DNA polymerase I Klenow fragment, 0.5 mM ATP and 2 units of T4 DNA ligase, and reaction was carried out at 37° C. for 3 hours, and at 25° C. for 2 hours, whereafter the reaction was stopped by adding 2 µl of 0.2 mM EDTA. The reaction product was used to transform infectable JM 105 cells; the transformant cells were allowed to grow overnight, whereafter an ssDNA was isolated from the culture medium supernatant. Using this ssDNA as a template for the 2nd cycle of primer elongation, gel-purified RF-type DNA was transformed into infectable JM 105 cells; the resulting transformant cells were spread over an agar plate, and were cultured overnight to obtain phage plaques.
(3) Site-directed mutagenesis The procedure of the above term (2) was repeated but the synthetic oligonucleotide primer used was: 5'-CGCCCATGGTGCCATCCTC-3' which produces in the base sequence a recognition site for the restriction enzyme NcoI, and concurrently changes Gly-9 to Thr and Ser-10 to Met, respectively:

(4) Site-directed mutagenesis

The procedure of the above term (2) was repeated but the synthetic oligonucleotide primer used was: 5'-TAACACCTTAAGAAGCCAG-3' which produces in the base sequence a recognition site for the restriction enzyme AflII, and concurrently changes the Lys-87-encoding codon to a termination codon.

(5) Site-directed mutagenesis

The procedure of the above term (2) was repeated but the synthetic oligonucleotide primer used was: 5'-CCGGACTCCGTTAACTCGG-3' which produces in the base sequence a recognition site for the restriction enzyme HpaI, and concurrently changes Asp-42 to Asn.

(6) Site-directed mutagenesis

The procedure of the above term (2) was repeated but the synthetic oligonucleotide primer used was: 5'-CTTCTCCTGGACTCCGTCAAC-3' which deletes the recognition site for the restriction enzyme HpaII in the base sequence, and concurrently changes Arg-45 to Gln.

(7) Screening and identification of plaques which were mutagenic

Plates containing mutated M13-PO plaques [above term (1)] and 2 plates containing unmutated M13-PO phage plaques were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl having a pH-value of 7.5 and 1.5M NaCl. The filters were twice washed on filters immersed in 2×SSC (Standard Sodium Citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. Each filter was washed at 50° C. for 30 minutes in a buffer solution for washing containing 0.1% SDS and a reduced amount of SSC. The filters were then first washed with a buffer solution containing 2×SSC; the control filters, which contained unmutated M13-PO plaques, were examined for radioactivity using a Geiger counter. While stepwise reducing SSC concentration, the control filters, which contained unmutated M13-PO plaques, were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-PO plaques and 100 unmutated control plaques by means of an oligonucleotide probe treated with $^{32}$P-γ-ATP. None of the control plaques hybridized to the probe, while 3 to 10 of the mutated M13-PO plaques hybridized to the probe.

One of the mutated M13-PO plaques was taken, and was inoculated to a JM105 culture medium. From the resulting supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the GGC (Gly-9) codon had been changed to an ACC (Thr) codon and the AGC (Ser-10) codon had been changed to an ATG (Met) codon; the CCG (Pro-14) codon, to an ATG (Met) codon; the AAA (Lys-87) codon, to a TAA (termination) codon; the GAC (Asp-42) codon, to an AAC (Asn-42) codon; and the CGG (Arg-45) codon, to a CAG (Gln-45) codon.

Of the mutated M13-PO phages, the phage in which Gly-9 codon had become a Thr-encoding codon and the Ser-10 codon had become a Met-encoding codon was named M13-PN10;

the phage in which the Pro-14 codon had become a Met-encoding codon, M13-PN14;

the phage in which the Lys-87 codon had become a termination codon, M13-PC86;

the phage in which the Asp-42 codon had become an Asn-encoding codon, M13-PDN42; and, the phage in which the Arg-45 codon had become a Gln-encoding codon, M13-PRQ45.

Reference Example 12

(Expression in *Escherichia coli* of gene which encodes human bFGF mutein)

(1) Construction of the plasmid pTB795 for human bFGF mutein expression

The M13-PN14 replicative form (RF) obtained in Example 11 above was treated in the manner described in Reference Example 5 (1) to construct the plasmid pTB795 for human bFGF mutein.

Using this plasmid pTB795, *Escherichia coli* MM294 was transformed, whereby the strain *Escherichia coli* MM294/pTB795 (IFO 14700, FERM BP-1660) was obtained, which contains the plasmid pTB795 containing the mutein-encoding gene.

(2) Preparation of bacterial cell extract

The above-mentioned transformant was cultured by the method described in Reference Example 5 (2) to give a supernatant, which was then used as a bacterial cell extract.

(3) Human bFGF activity of the bacterial cell extract

A determination was made of the human bFGF activity of the bacterial cell extract obtained in (2) above, by the method described in Reference Example 5 (3).

The bacterial cell extract from *E. coli* MM294/pTB795 thereby tested exhibited FGF activity. The mutein N14, in which the amino acid sequence of from Pro at the 2-position to Pro at the 14-position of human bFGF had been deleted, was thus obtained.

Reference Example 13

(Expression in *Escherichia coli* of gene which encodes human bFGF mutein)

(1) Construction of the plasmid pTB796 for human bFGF mutein expression

The M13-PC86 replicative form (RF) obtained in Reference Example 11 above was treated in the manner described in Reference Example 5 (1) to construct the plasmid pTB796 for human bFGF mutein.

Using this plasmid pTB796, *Escherichia coli* MM294 was transformed, whereby the strain *Escherichia coli* MM294/pTB796 (IFO 14701, FERM BP-1661) was obtained, which contains the plasmid pTB796 containing the mutein-encoding gene.

(2) Preparation of bacterial cell extract

The above-mentioned transformant was cultured by the method described in Reference Example 5 (2) to give a supernatant which contains the mutein C86, in which the amino acid sequence of from Lys at the 87-position to Ser at the 147-position had been deleted, and the supernatant was then used as a bacterial cell extract.

Reference Example 14

(Expression in *Escherichia coli* of gene which encodes human bFGF mutein)
(1) Construction of the plasmid pTB797 for human bFGF mutein expression The M13-PDN42 replicative form (RF) obtained in Reference Example 11 above was treated in the manner described in Reference Example 5 (1) to construct the plasmid pTB797 for human bFGF mutein.

Using this plasmid pTB797, *Escherichia coli* MM294 was transformed, whereby the strain *Escherichia coli* MM294/pTB797 (IFO 14702, FERM BP-1662) was obtained, which harbors the plasmid pTB797 containing the mutein-encoding gene.
(2) Preparation of bacterial cell extract The above-mentioned transformant was cultured by the method described in Reference Example 5 (2) to give a supernatant, which was then used as a bacterial cell extract.
(3) Human bFGF activity of the bacterial cell extract A determination was made of the human bFGF activity of the bacterial cell extract obtained in (2) above, by the method described in Reference Example 5 (3).

The bacterial cell extract from *E. coli* MM294/pTB797 thereby tested exhibited FGF activity. The mutein DN42, in which Asp at the 42-position of human bFGF had been replaced by Asn, was thus obtained.

Reference Example 15

(Expression in *Escherichia coli* of gene which encodes human bFGF mutein)
(1) Construction of the plasmid pTB855 for human bFGF mutein expression The DNA of the plasmid pTB669 which was obtained in the above mentioned Reference Example 2 was cleaved with a restriction enzyme HincII, and it was ligated with EcoRI linker p(5'CATGAATTCATG 3') under T4 DNA ligase reaction. Thus obtained DNA was further cleaved with a restriction enzymes EcoRI and PstI to recover a DNA fragment of about 0.35 kb. This DNA fragment was ligated with the about 3.2 kb DNA fragment obtained in Reference Example 5 (1), the fragment being obtained by cleaving the plasmid ptrp781 with EcoRI-PstI, to obtain the plasmid pTB855 for human bFGF mutein expression was constructed.

Using this plasmid 855, *Escherichia coli* MM294 was transformed, whereby the strain *Escherichia coli* MM294/ pTB855, which contains the plasmid pTB855 having the mutein-encoding gene.
(2) Preparation of bacterial cell extract The above-mentioned transformant was cultured by the method described in Reference Example 5 (2) to give a supernatant, which was then used as a bacterial cell extract.
(3) Human bFGF activity of the bacterial cell extract A determination was made of the human bFGF activity of the bacterial cell extract obtained in (2) above, by the method described in Reference Example 5 (3).

The bacterial cell extract from *E. coli* MM294/pTB855 thereby tested exhibited FGF activity. The mutein N41, in which the amino acid sequence of from Pro at the 2-position to Val at the 41-position of human bFGF had been deleted, was thus obtained.

Reference Example 16

(Expression in *Escherichia coli* of gene which encodes human bFGF mutein)
(1) Construction of the plasmid pTB856 for human bFGF mutein expression The DNA of the plasmid pTB669 which was obtained in the above mentioned Reference Example 2 was partly cleaved with a restriction enzyme BamHI so as to obtain BamHI recognition site in the bFGF gene. The site was further cleaved with *Escherichia coli* DNA polymerase I in the presence of dATP, dCTP, dGTP, dTTP to give blunt end. This DNA is ligated with NheI linker p(5'CTAGCTAGCTAG3') under T4 DNA ligase reaction. After treating with the restriction enzyme NheI and ligating the cleaved site under T4 DNA ligase reaction, the plasmid pTB856 for human bFGF mutein expression was constructed.

Using this plasmid pTB856, *Escherichia coli* MM294 was transformed, whereby the strain *Escherichia coli* MM294/pTB856 which contains the plasmid pTB856 having the mutein-encoding gene.
(2) Preparation of bacterial cell extract The above-mentioned transformant was cultured by the method as in Reference Example 5 (2) to give a supernatant which contains the mutein C129, in which the amino acid sequence of from Lys at the 130-position to Ser at the 147-position had been deleted, was thus obtained, and then the supernatant which was then used as a bacterial cell extract.

Reference Example 17

(Production of H-Leu-Pro-Met-Ser-Ala-Lys-Ser-OH)

Boc-Ser(Bzl)-resin (696 mg, 0.72 m mol/g resin) was applied to automatic peptide synthesizer Type 430A (Applied Biosystems, U.S.A.), and the following amino acids were applied to the synthesizer in that order so as to cause condensation reaction:
Boc-Lys(Z)-OH, Boc-Ala-OH, Boc-Ser(Bzl)-OH, Boc-Met-OH, Boc-Pro-OII,
Boc-Leu-OH
Bzl: benzyl
Boc: t-butoxycarbonyl
Z: benzyloxycarbonyl By said procedure, 1.08 g of Boc-Leu-Pro-Met-Ser(Bzl)-Ala-Lys(Z)-Ser(Bzl)-resin was produced. 400 mg of the peptide-resin was incubated in 5.0 ml of hydrogen fluoride containing 0.5 ml of anisole and 0.5 ml of dimethylsulfide at 0° C. for 60 minutes to recover the peptide from resin. The excess amount of hydrogen fluoride was removed by distillation under reduced pressure to give a residue. The residue was washed with diethyl ether, and extracted with 30 ml of water, and lyophilized. The lyophylizate was dissolved in 5 ml of water, and the solution was subjected to ion-exchange employing Amberlite IRA-400 (acetate form) resin (column 2×5 cm, elution solvent: water). The eluate was concentrated under reduced pressure, and subjected to gel filtration with Sephadex LH-20 (Pharmacia, column 2.5×125 cm, elution solvent: 1N acetic acid) to obtain the peptide H-Leu-Pro-Met-Ser-Ala-Lys-Ser-OH.

Yield: 118 mg (78.8%)
Rf value: 0.22 (ethyl acetate:acetic acid:butanol:water= 1:1:1:1)
$[\alpha]_D^{25}$ –8.1 (c=0.11, 1N acetic acid)
Amino acid analysis: Ser. 2.08, Pro 1.06, Ala 1.00, Met 0.98, Leu 1.03, Lys 0.99.

Example 1

(Immunization)

BALB/c mice (female, 4-week old) had the antigen human bFGF (as obtained in Reference Example 3) in solution in 0.4 ml of Freund's complete adjuvant (Difco Laboratories, U.S.A.) injected intraperitoneally. Three weeks later, 10 µg of the antigen hbFGF in solution in 0.4 ml of Freund's incomplete adjuvant was intraperitoneally administered. 3 weeks later, the same additional immunization was carried out, and two weeks later, 10 µg of human bFGF in saline was intraperitoneally inoculated.

Example 2

(1) Cell fusion

From the immunized mice mentioned in Example 1, the spleen was excised 4 days after final antigen challenge to thereby obtain cells to be used for cell fusion. These cells were suspended in a medium prepared by mixing together Isokov medium and Ham F-12 medium in a ratio of 1:1 (hereinafter referred to as IH medium).

The mouse myeloma cell P3-X63-Ag 8UI was subcultured in RPMI 1640 medium containing 10% fetal bovine serum under an atmosphere of 5% carbon dioxide and 95% air.

Cell fusion was conducted in accordance with the method established by Kohler and Milstein [Kohler, G. and Milstein, C.: Nature, 256, 495 (1975)]. $2.9 \times 10^7$ cells of the above myeloma cell line and $1.5 \times 10^8$ immunized lymphocytes obtained by the above-mentioned method were mixed together and centrifuged, and 45% polyethylene glycol 6000 (hereinafter referred to as PEG 6000) in 0.3 ml of IH medium was dropwise added. The PEG 6000 solution was preheated to 37° C., and was gradually added. Five minutes later, the 37° C.-preheated IH medium was added at a rate of 0.5 ml per minute to make 10 ml. The solution was then centrifuged at room temperature at 600 rpm for 15 minutes, and the supernatant was removed. This cell precipitate was suspended in 200 ml of IH medium containing 20% calf serum, and this suspension was transferred to a 24-well microplate (Linbro) in an amount of 2 ml per well. One day later, IH medium (containing 20% calf serum) supplemented with HAT ($1 \times 10^{-4}$M hipoxanthine, $4 \times 10^{-7}$M aminopterin, $1.6 \times 10^{-5}$M thymidine) (hereinafter referred to as HAT medium) was added to the microplate in an amount of 1 ml per well, and, a further three day, one half amount of the medium was replaced with HAT medium. The cells thus grown are hybrid cells.

(2) Search for antibody-producing cells

Previously, the hybridoma conditioned medium was added in an amount of 100 µl per well to a 96-well polystyrene microtiter plate which had had human bFGF immobilized thereto, and incubation was carried out at room temperature for 2 hours. The medium was removed, and, after washing, the horse radish peroxidase (HRP)-labeled anti-mouse IgG goat antibody (Miles) was added as the secondary antibody, and incubated at room temperature for 2 hours. The secondary antibody was removed, and, after thoroughly washing the wells, coloring reaction was carried out in the presence of added reaction substrate (EIA method). By this method potent valency was observed in 3 wells.

(3) Cloning of hybrid cells

Cells in each of these three cells were sown to 0.5 cell per well to a 96-well microtiter plate which had had $10^4$ cells/well mouse thymocytes as vegetative cells sown thereon, and cloning was carried out. As a result, three clones, namely the mouse HbF99 cell (IFO 50122), the mouse HbF161 cell (IFO 50123) and the mouse HbF165 cell (IFO 50124) were obtained.

The results of the determination of antibody titers in supernatants of these cell lines are shown in Table 2.

TABLE 2

| Dilution | Culture Supernatant | | | Parent Line Myeloma Cell | bFGF-Immunized Mouse Serum |
|---|---|---|---|---|---|
| | HbF 99 | HbF 161 | HbF 165 | | |
| ×64 | 1.93 | 1.08 | 0.66 | 0.02 | — |
| ×128 | 1.72 | 0.63 | 0.51 | 0.02 | — |
| ×3200 | — | — | — | — | 1.93 |
| ×6400 | — | — | — | — | 1.25 |

Note: The numerical figures in the above Table 2 represent absorbances at 492 nm wavelength; blank (—) means that determination was not made.

The cloned cells were stored in IH medium containing 20% calf serum and having dimethylsulfoxide (DMSO) added thereto to 10% under liquid nitrogen atmosphere.

Example 3

(Immunoglobulin class of monoclonal antibodies)

The mouse antibodies obtained in Example 2 were reacted with various immunoglobulin standards by means of the Mouse-Typer subisotyping kit (Bio-Rad). The results are presented in Table 3.

TABLE 3

| Immunoglobulin Standard | Monoclonal Antibodies According to the Invention | | |
|---|---|---|---|
| | MoAb99 | MoAb161 | MoAb165 |
| IgG 1 | − | − | − |
| IgG 2a | − | − | − |
| IgG 2b | − | − | − |
| IgG 3 | − | − | − |
| IgM | + | + | + |
| IgA | − | − | − |

Note: + indicates positive for the reaction, and − indicates negative for the reaction.

From Table 2 it is obvious that HbF99, HbF161, and HbF165, all belong to the immunoglobulin class IgM.

Example 4

Spleens were collected from BALB/c mice immunized by the method described in Example 1, and, by the methods described in Example 2 (1), (2) and (3), the hybridomas HbF12 (IFO 50142), HbF45, HbF47, HbF52 (IFO 50143), HbF78 (IFO 50144) and HbF98 (IFO 50145) were obtained. $2 \times 10^6$ cells each hybridoma were intraperitoneally inoculated to mice to which 0.5 ml of mineral oil were preinjected.

After 10 days, 2 to 4 ml of ascites per mouse were collected, and monoclonal antibodies MoAb12, MoAb45, MoAb47, MoAb52, MoAb78 and MoAb98 were obtained, from said hybridomas, respectively, in accordance with the method described in Example 2 (4).

By the method described in Example 3, determinations were made of the immunoglobulin class of said monoclonal antibodies, whereby the following results shown in Table 4 were obtained.

TABLE 4

| Monoclonal Antibody | Immunoglobulin Class |
|---|---|
| MoAb12 | IgG 1 |
| MoAb45 | IgG 1 |
| MoAb47 | IgM |
| MoAb52 | IgG 2b |
| MoAb78 | IgG 2b |
| MoAb98 | IgG 1 |

Example 5

(1) Preparation of radiolabeled hbFGF

Using the transformant *Escherichia coli* MM294/pTB669 (IFO 14532, FERM BP-1281) described in Reference Example 2, hbFGF radiolabeled with $^{35}$S was obtained in the following manner.

The above *Escherichia coli* MM294/pTB669 was cultivated in the medium described in Reference Example 3 until the Klett value was 200. This culture broth in the one fifth amount was poured into M9 (Met$^-$) medium. The M9 (Met$^-$) medium was prepared by supplementing the M9 medium containing 1% glucose, 8 μg/ml tetracycline, and the amino acid shown below:

| Amino acid composition | |
|---|---|
| L-alanine | 25.0 mg/l |
| L-arginine hydrochloride | 84.0 mg/l |
| L-asparagine monohydrate | 28.4 mg/l |
| L-aspartic acid | 30.0 mg/l |
| L-cysteine disodium salt | 82.8 mg/l |
| L-glutamic acid | 75.0 mg/l |
| L-glutamine | 584.0 mg/l |
| L-glycine | 30.0 mg/l |
| L-histidine hydrochloride monohydrate | 42.0 mg/l |
| L-isoleucine | 105.0 mg/l |
| L-leucine | 105.0 mg/l |
| L-lysine hydrochloride | 146.0 mg/l |
| L-phenylalanine | 66.0 mg/l |
| L-proline | 40.0 mg/l |
| L-serine | 42.0 mg/l |
| L-threonine | 95.0 mg/l |
| L-tyrosine | 83.9 mg/l |
| L-valine | 94.0 mg/l |

Cultivation was carried out in the M9 (Met$^-$) medium until the Klett value was 200, and 3-β-indoleacrylic acid was added to 25 μg/ml, and the cultivation was continued for 2 more hours. Thereafter, a 1-ml portion of the culture broth was collected, and 10 μCi of $^{35}$S-Met (specific activity >1000 Ci/mmol) was added, and cultivation was carried out for 30 minutes. After cultivation, cells were harvested, and a cell extract was obtained in accordance with the method described in Reference Example 3.

The *Escherichia coli* MM294 carrying the vector plasmid ptrp781 and described in Reference Example 2 was subjected to the same procedure to thereby obtain a labeled cell extract.

(2) Imnunoprecipitation

A 10% solution of Protein A (BRL) was prepared in accordance with the instruction manual thereof. An unlabeled *Escherichia coli* cell extract was obtained by treating *Escherichia coli* MM294/ptrp781 by the method of Reference Example 3.

One milliliter of the ascites fluid obtained in Example 4 was mixed with 100 μl of the unlabeled *Escherichia coli* cell extract, and the mixture, after being allowed to stand at 4° C. for 1 hour, had $10^6$ cpm of the labeled cell extract (MM294/ptrp781 or MM294/pTB669) added thereto, and was allowed to stand at 4° C. overnight.

To 100 μl of the 10% solution of Protein A, was added 100 μl of the unlabeled *Escherichia coli* cell extract, and the mixture, after being allowed to stand at 4° C. overnight, was centrifuged and again suspended in 100 μl of NETBN solution [150 mM NaCl, 5 mM EDTA, 50 mM Tris-HCl (pH 7.5), 0.1% BSA, 0.05% Non-idet (NP)-40]. To this suspension was added the above-treated mixture of labeled cell extract of ascites, and the mixture was allowed to stand at 4° C. overnight. This mixture was then centrifuged, and the resulting precipitate was suspended in 500 μl of NETBN solution. This procedure was repeated 5 times to thereby remove unadsorbed labeled substance, and the pellets were resuspended with 50 ml of electrophoresis sample buffer. The polyacrylamidegel electrophoresis was performed in accordance with the method of Laemmli, U. K. [Nature, 227, 680 (1970)]. After migration, the gel was immersed in 50% trichloroacetic acid (TCA) for 1 hour and was washed four times with distilled water for 30 minutes for each wash to thereby remove the TCA, after which the gel was immersed in dimethylsulfoxide (DMSO) for 1 hour. Thereafter, the gel was immersed in DMSO containing 10% 2,5-diphenyloxazole (DPO) for 1 hour. After washing three times with distilled water for 30 minutes for each wash, the gel was dried. The dried gel was radioautographed, and the immnunoprecipitation pattern was examined. The radioautograms are shown in FIG. 2. From FIG. 2, the monoclonal antibodies MoAb12, MoAb52, MoAb78 and MoAb98 were found to combine with hbFGF in cell extract.

Example 6

The antibody valencies of the 4 lines which showed immunoprecipitation in example 5, selected from the monoclonal antibodies described in Example 4, namely the monoclonal antibodies MoAb12, MoAb52, MoAb78 and MeAb 98 were determined by the limiting dilution method.

Figure 3:
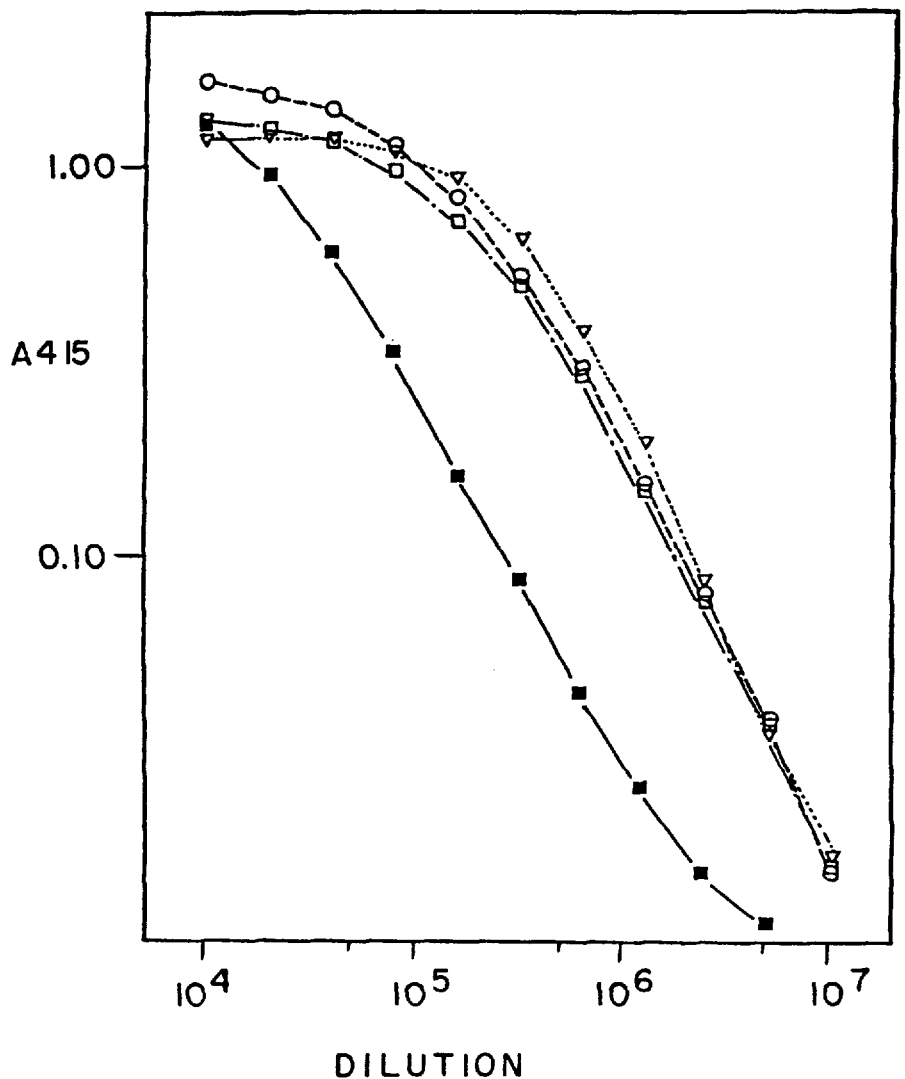
FIG. 3 shows the antibody valencies as obtained in Example 6.

That is, each of the ascites fluids of monoclonal antibody MoAb12, MoAb52, MoAb78 or MoAb98 obtained in Example 4 was diluted with IH medium containing 10% fetal bovine serum, and the quantity of antibodies in the dilution was determined by the EIA method mentioned in Example 2 (2). The results are shown in FIG. 3. In FIG. 3, - - - β - - - indicates the results for MoAb12, - - - □ - - - indicates the results for MoAb52, - - - ■ - - - indicates the results for MoAb78, and - - - ▽ - - - indicates the results for MoAb98.

FIG. 3 shows that the ascites containing the above antibody show a limiting dilution rate of more than $1 \times 10^6$, that is, these 4 antibodies are very high in antibody valency.

Example 7

(Determination of recognition site to the antigen)

Recognition sites of the four antibodies, which show high antibody valencies obtained in Example 6, to the antigen were determined by competitive analysis.

As competitors, hbFGF obtained in Reference Example 3, synthetic peptide Pep 1: Pro-Ala-Leu-Pro-Glu-Asp-Gly-Gly-Ser-Thr (which is obtained by adding Tyr to the polypeptide of N-terminal amino acids Nos. 2 to 10, Regulatory Peptides, 10, 309–317(1985)), synthetic peptide Pep 2: Leu-Pro-Met-Ser-Ala-Lys-Ser (which corresponds to the amino acids Nos. 142 to 147 obtained in Reference Example 17), bFGF mutein N14 (obtained in Reference Example 12), and bFGF mutein N41 (obtained in Reference Example 15).

The synthetic peptides were adjusted to the concentration of 100 μg/ml and diluted with IH medium (Iscov and Ham F12 mixed medium at a ratio with 1:1) containing 10% FCS.

Figure 4:
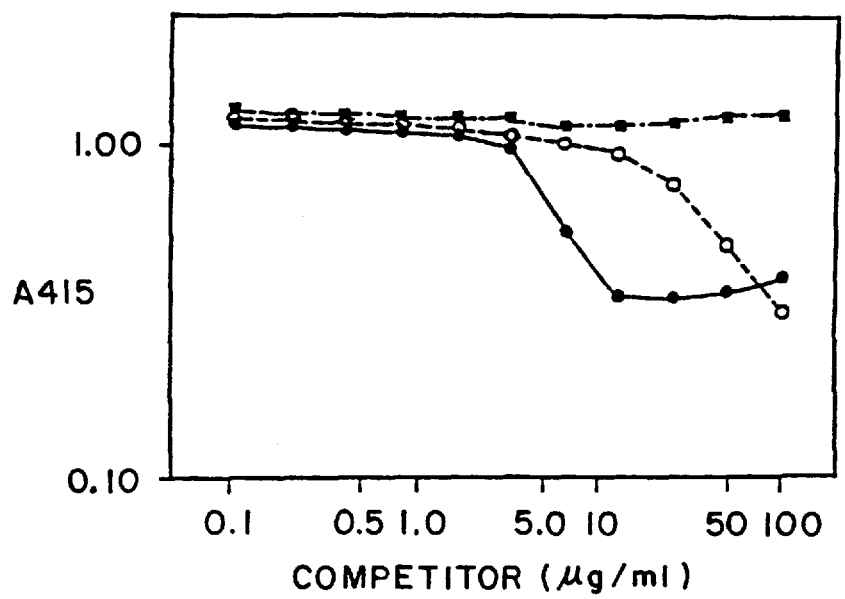
FIG. 4 shows the results of competitive inhibition experiment to MoAb12 by the various peptides as obtained in Example 7.
Figure 5:
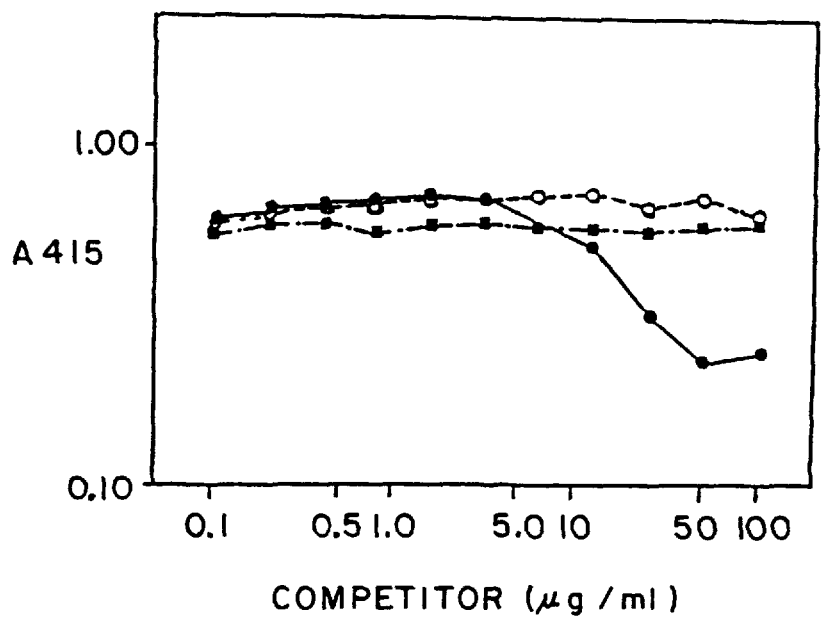
FIG. 5 shows the results of competitive inhibition experiment to MoAb52 by the various peptides as obtained in Example 7.
Figure 6:
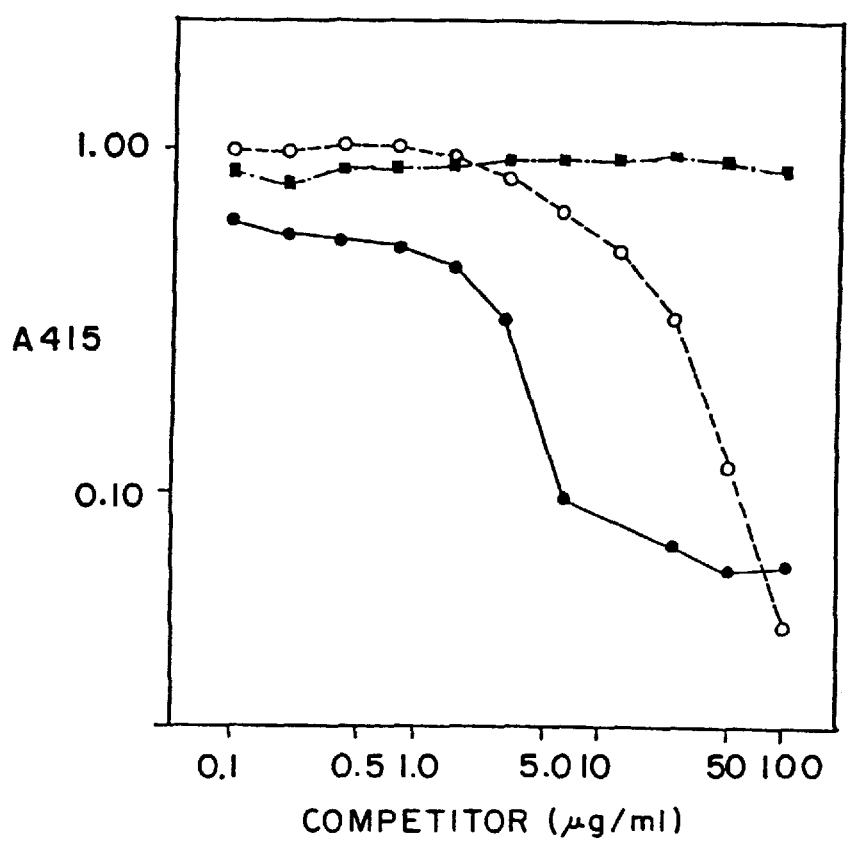
FIG. 6 shows the results of competitive inhibition experiment to MoAb78 by the various peptides as obtained in Example 7.
Figure 7:
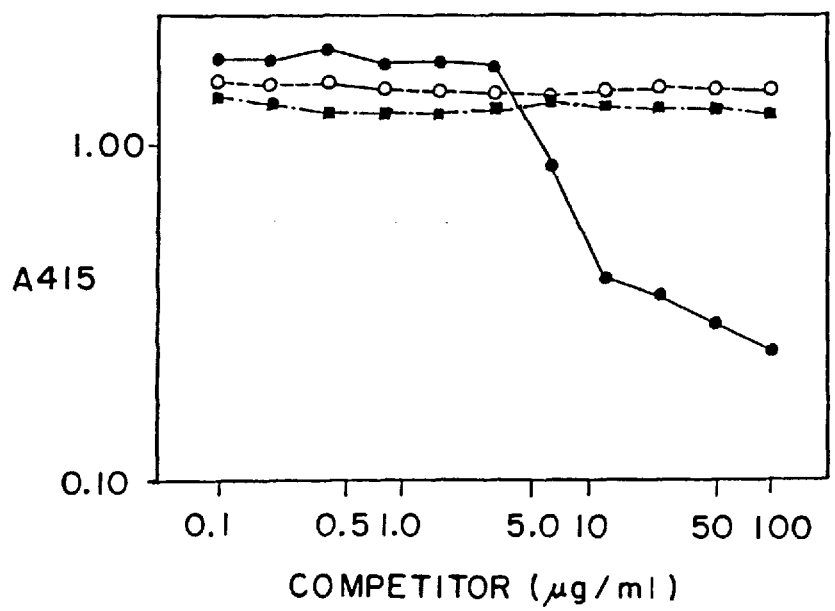
FIG. 7 shows the results of competitive inhibition experiment to MoAb98 by the various peptides, as obtained in Example 7.

The extract containing the mutein N14 or N41 obtained in Reference Example 12 (2) or 15 (2) was diluted with IH medium containing 10% FCS. The antibodies, obtained in Example 4, were diluted to their binding titers showing between 0.7 and 1.0 with absorbance at 415 nm. So, dilution factor about MoAb12, MoAb52 and MoAb98 was $5 \times 10^5$, and about MoAb98 was $5 \times 10^4$. In the above dilution, IH medium containing 10% FCS was used as a diluent. To the diluted antibody solution were added the diluted competitor. After stirring the mixture, the diluent was warmed at 37° C. for 30 minutes. The amount of the unbound antibody was measured by EIA method shown in Example 2 (2). The results in case of using synthetic peptide are shown in FIGS. 4 to 7. FIG. 4 shows the results on the monoclonal antibody MoAb12, FIG. 5 shows the results on the monoclonal antibody MoAb52, FIG. 6 shows the results on the monoclonal antibody MoAb 78, and FIG. 7 shows the results on the monoclonal antibody MoAb98.

In these figures, - - - ● - - - denotes the results of hbFGF, - - - ○ - - - denotes the results of Pep 1, - - - ■ - - - denotes the results of Pep 2, these being used as competitor, and the vertical axis denotes the absorption at 415 mm.

As shown in the FIGS. 4 and 6, the monoclonal antibodies MoAb12 and MoAb78 are competitively inhibited to combine with bFGF and Pep 1. This indicates that the monoclonal antibodies MoAb12 and MoAb78 recognize the N-terminal amino acids of Nos. 2 to 10.

As shown in the FIG. 5 and FIG. 7, the monoclonal antibodies MoAb52, MoAb98 are not competitively inhibited to Pep 1 and Pep 2.

Figure 8:
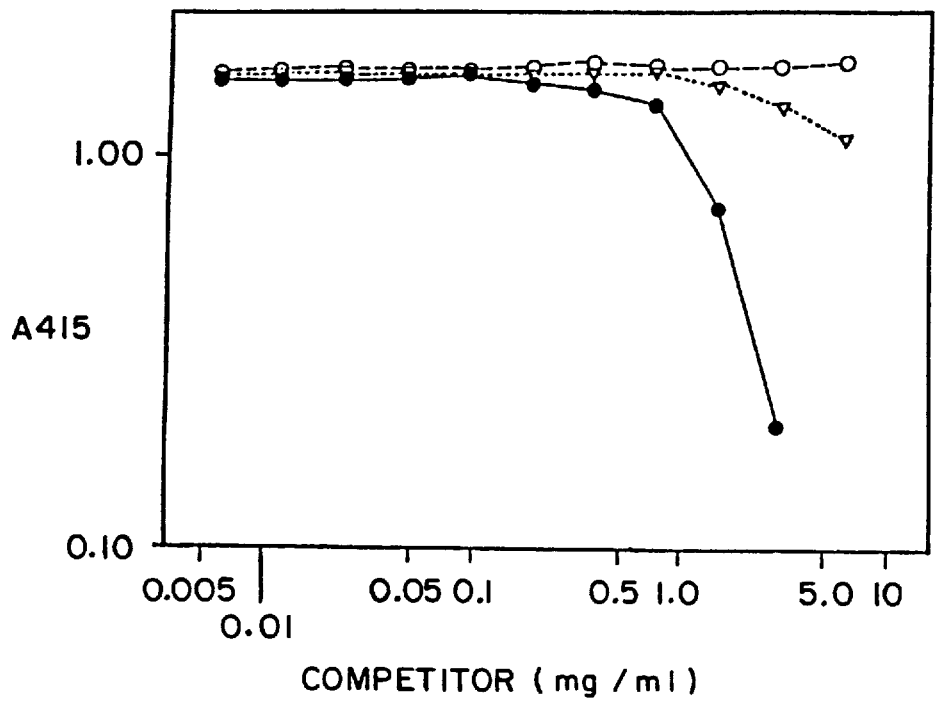
FIG. 8 shows the results of competitive inhibition experiment on bFGF mutein of MoAb52 as obtained in Example 7.
Figure 9:
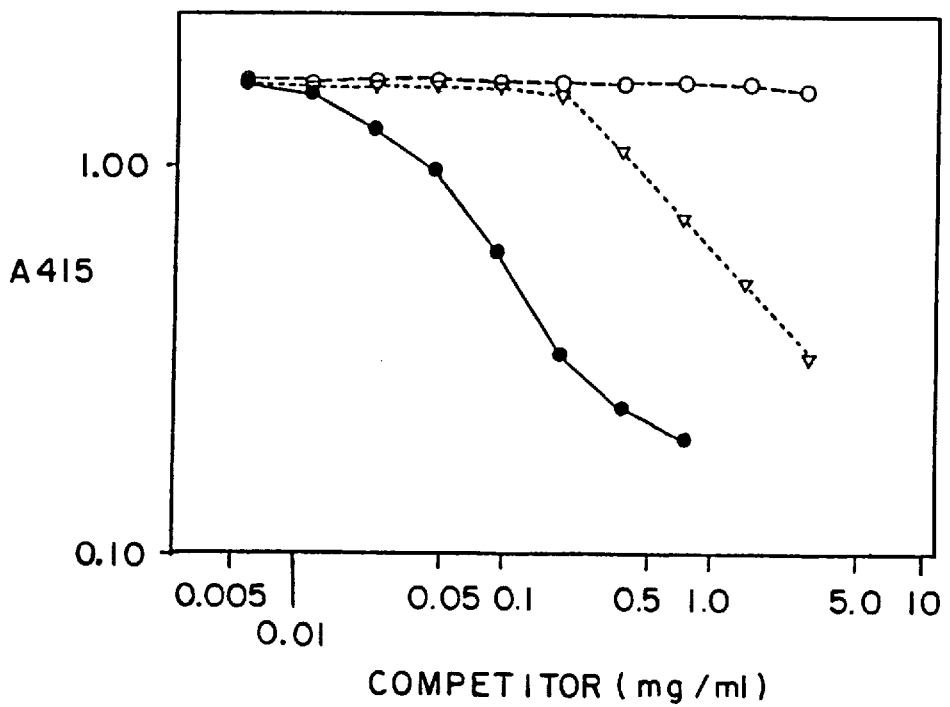
FIG. 9 shows the results of competitive inhibition experiment on bFGF mutein of MoAb as obtained in Example 7.

In order to determine the recognition site of the monoclonal antibodies, the competition analyses were conducted using the mutein N14 (obtained in Reference Example (2) or N41 (obtained in Reference Example 15) by the method described in the above, and the results are shown in FIGS. 8 and 9. In these figures, - - - ● - - - denotes the results of hbFGF, - - - ▽ - - - denotes the results of the mutein N14, - - - ○ - - - denotes the results of the mutein N41, and the vertical axis denotes the absorption at 415 mm, and the horizontal axis shows the total protein in the *E. coli* extract obtained in Reference Example 3.

As shown in FIG. 8 and FIG. 9, the monoclonal antibodies MoAb52 and MoAb98 are competitively inhibited to combine with mutein N14, but not with mutein N41. This indicates that the monoclonal antibodies MoAb52 and MoAb98 recognize the amino acids of Nos. 15 to 41.

The competitive analysis was carried out on bovine acidic FGF (baFGF) [purchased from R & D Systems Inc., U.S.A.] and human bFGF obtained in Reference Example 3 by the method described in the above, and the results are shown in Table 5. The results are indicated by optical density of the substrate by EIA method.

TABLE 5

|  | baFGF | | hbFGF | |
| --- | --- | --- | --- | --- |
|  | 10 µg/ml | 80 ng/ml | 10 µg/ml | 80 ng/ml |
| MoAb12 | 1.049 | 0.975 | 0.396 | 1.077 |
| MoAb52 | 0.997 | 0.923 | 0.230 | 0.722 |
| MoAb78 | 0.978 | 0.962 | 0.062 | 0.523 |
| MoAb98 | 0.948 | 0.921 | 0.095 | 1.356 |

As shown in Table 5, the monoclonal antibodies MoAb12, MoAb52, MoAb78 and MoAb98 do not cross-react with bovine bFGF.

All of the above results are shown in the following Table 6.

TABLE 6

| | Monoclonal Antibody HbF | | | |
| --- | --- | --- | --- | --- |
| | 12 | 52 | 78 | 98 |
| hbFGF | + | + | + | + |
| baFGF | − | − | − | − |
| N14 | − | + | − | + |
| N41 | − | − | − | − |
| Pep1 | + | − | + | − |
| Pep2 | − | − | − | − |

In the Table 6, + denotes that they are competitive, and − denotes that they are not competitive.

Example 8

(Purification of the monoclonal antibody from ascites)

The monoclonal antibody MoAb12, MoAb52, MoAb78 or MoAb98 was inoculated to 10 mice, and 20 to 30 ml of ascites were collected. The ascites were subjected to centrifugation at 2,000 rpm (Hitachi refrigrated centrifuge) to remove cells, and further subjected to centrifugation with Spinco SW 28 roter (Beckman, U.S.A.) at 4° C. for 2 hours to remove the insoluble proteins and fats. To the supernatant thus obtained there is added ammonium sulfate so as to 40% saturation, and the mixture was stirred gently in ice bath for 1 hour.

The precipitate was subjected to centrifugation with Sorval SS34 roter (Dupont, U.S.A.) at 4° C., 15,000 rpm. The pellet was dissolved in Buffer 1 [20mM Tris.HCl (pH 7.9), 40 mM NaCl] so that the protein concentration is 10 to 15 mg/ml. Thus obtained solution is dialyzed for the Buffer 1 at 4° C. overnight. Thus obtained solution is passed through the column of DEAE-cellulose (DE-52, Whatman, U.S.A.) to adsorb. The elution was carried out employing the linear gradient from Buffer 1 to 0.4M NaCl.

The immunoglobulin fractions were recovered. To the fraction were added 40% saturated ammonium sulfate so as to emerge precipitate. The precipitate was dissolved in Buffer 2 (0.1M NaHCO$_3$) so as to the protein concentration being 10 to 20 mg/ml, and the solution was subjected to dialysis to Buffer 2 at 4° C. for two overnights. The Buffer 2 were replaced every day.

Furthermore, the dialyzate is subjected to hydroxy apatite column (HCA column). As the initiation buffer, 10 mM sodium phosphate buffer (pH 6.8) was used, and as the elution buffer, 5mM sodium phosphate buffer (pH 6.8) was used. The elution was carried out by linear gradient elution from the initial buffer to the elution buffer. Thus obtained eluate containing the antibody was preserved at 4° C.

Example 9

(Purification of hbFGF by antibody column)

5 ml of Affi-Gel-10 (Bio-Rad, U.S.A.) was put on sintered filter, was washed with ten volumes of ice-cooled isopropanol and with ten times of ice-cooled distilled water. Thus obtained gel is transfered to a reaction vessel. To the gel was mixed with 15 mg of monoclonal antibody MoAb78 in the volume of 5 to 15 ml (dissolved in Buffer 2 or phosphate buffer, in Example 8) to react at 4° C. overnight.

Monoethanol amine (pH 8.0) was added to the reaction mixture with the concentration of 0.01M, and leave at room temperature for one hour to inactivate the unreacted site. The gel was washed with 10 times (volume) of Buffer 2 (Example 8). 2 ml of the gel was packed into a column, and the column was equilibrated with the initiation buffer [20mM Tris.HCl (pH 7.6), 1 mM EDTA, 0.15M NaCl, 0.05% NP-40].

On the other hand, the extracts of a transformant *Escherichia coli* DH1/pTB744 (the extracts containing mutein CS4), is diluted three times by the addition of the initial buffer. The diluent was applied to said column at a flow rate of 20 ml/hour to adsorb the mutein CS4 to the antibody. After the adsorption, the column was washed with 20 ml of the initial buffer, and then the elution was carried out by using 20 ml of high salt buffer [20 mM Tris.HCl (pH 7.6), 1 mM EDTA, 1M NaCl, 0.05% NP-40], 20 ml of an elution buffer A [0.2M acetate buffer (pH 4.5), 0.2M NaCl], 20 ml of an elution buffer B [0.2M acetic acid (pH 2.5), 0.2M NaCl] in that order, wherein the flow rate is 20 ml/hour and the temperature is 4° C. Thus obtained fractions were subjected to electrophoresis in accordance with the method described in Laemmli, Nature 277, 680 (1970) employing 17.25% acrylamide. Proteins were detected by silver staining.

Figure 10:
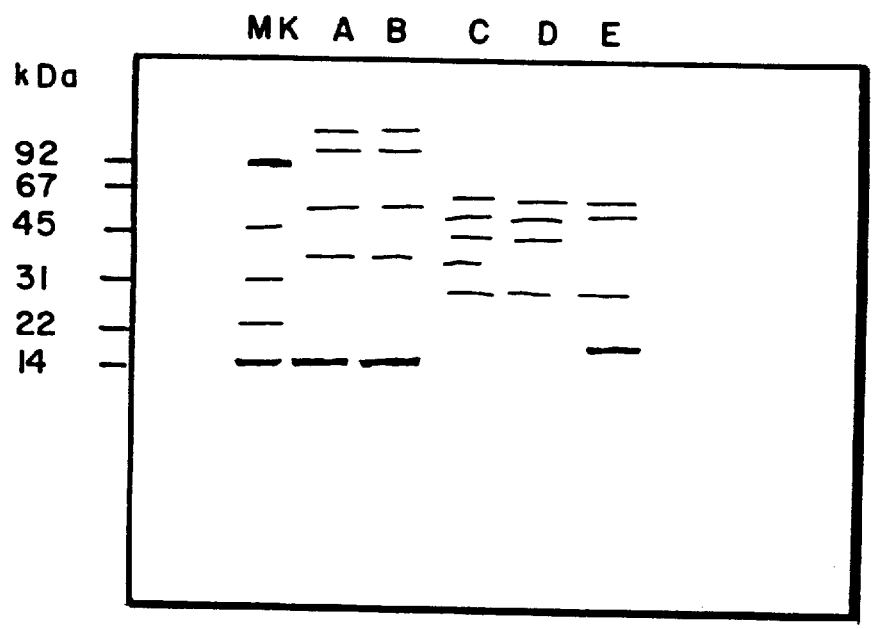
FIG. 10 shows the pattern of polyacrylamide gel electrophoresis as obtained in Example 9.

The results are shown in FIG. 10. In FIG. 10, MK denotes the result of molecular marker, A denotes that of the crude extract, B denotes that of flow through fractions, C denotes that of the eluent of the high salt buffer, D denotes that of the elution buffer A, and E denotes that of the elution buffer B. Just after the elution, the pH of D fraction and E fraction was adjusted to pH 7.5 by adding 1M Tris.HCl (pH 9.5). The FGF activity on the fractions were measured in accordance with the method of Reference Example 5 (3). The results are shown in Table 7. In Table 7, A to E denote the same as above.

TABLE 7

|   | Protein (A) ($\mu$g) | FGF Activity* (B) ($\mu$g) | B/A |
|---|---|---|---|
| A | 63000 | 96 | 0.0015 |
| B | 63000 | 19 | 0.0003 |
| C | 28 | 0.003 | 0.0011 |
| D | 17 | 0.049 | 0.0030 |
| E | 33 | 23 | 0.69 |

Note: *: The FGF activity is shown in equivalent amount of the bovine pituitary derived bFGF (perchared from Takara Shuzo, Japan) on the basis of incorporation of $^3$H-thymidine.

Example 10

(Measurement of hbFGF mutein by EIA method using monoclonal antibody)
(1) The antibody MoAb78 obtained in Example 4 was subjected to purification from ascites fluid in accordance with the method of Example 8. Thus obtained antibody was concentrated to more than 2 mg/ml, and subjected to dialysis in 0.2M sodium phosphate buffer (pH 7.0). To thus obtained 1.4 ml solution of monoclonal antibody MoAb78 (concentration 2.8 mg/ml), 50 $\mu$l of S-acetylmercaptosuccinic anhydride (Aldrich Co., U.S.A.) dissolved in N,N'-dimethylformamide was added so as to reach the concentration of 11.5 mg/ml. The air in the reaction vessel is replaced by nitrogen gas. The vessel was sealed, and subjected to stirring so as to cause the reaction of introducing SH group. The unreacted S-acetylmercaptosuccinic acid anhydride was inactivated by the treatment for 10 minutes with 130 $\mu$l of 0.2M Tris.HCl (pH 7.0), 13 $\mu$l of 0.2M EDTA and 130 $\mu$l of 2M hydroxyamine (pH 7.0). The MoAb78 was recovered by gel filtration using a column packed with Sephadex G-25 (diameter 1 cm×80 cm, Pharmacia, Sweden) (flow rate: 20 ml/hour).
(2) 10 mg of horse radish peroxidase (HRP, Behringer Manheim, Grade I, West Germany) was dissolved in 1.4 ml of 0.1M phosphate buffer (pH 6.8). On the other hand, 14 mg of N-hydroxysuccinimide ester of N-(4-corboxy cyclohexyl methyl)maleimide was dissolved in 335 $\mu$l of DMF, and 100 $\mu$l of thus obtained solution was added to the HRP solution above mentioned. The air in the reaction vessel was replaced by nitrogen gas, and the vessel was sealed. After 1 hour reaction at room temperature, proteins of the portion of HRP introduced with maleimide group were recovered by gel filtration using a colomn packed with Sephadex G-25 as in the above (f).
(3) 6 ml of the portion of the monoclonal antibody MoAb78 introduced with SH group obtained in the above (1) and 2 ml of the portion of HRP introduced with maleimide group obtained in the above (2) were mixed, and the mixture was concentrated to 1 ml using collodion bag (Sartorius, West Germany) under reduced pressure at 4° C. for 20 hours. After the reaction, the unreacted HRP introduced with SH group was removed with the use of Ultrogel AcA44 (LKB Co., diameter 1 cm×80 cm, Sweden) column (flow rate: 10 ml/hour). In the eluates, the fraction containing 2.4 HRP/ antibody has the most high HRP number per antibody molecule. The product thus obtained was employed in the EIA in the following item (4).
(4) The monoclonal antibody MoAb52 was purified by the manner described in the above (1). The monoclonal antibody MoAb52 was diluted with PBS so as to be 10 $\mu$g/ml or 20 $\mu$g/ml, and the diluent was poured into Immunoplate (Nunc, Denmark) so as to be 100 $\mu$l/well. The plate was kept standing at 4° C. overnight to adsorb the monoclonal antibody MoAb52 to the plate. After removing the antibody which is not adsorbed, the plate was washed with PBS thrice, PBS containing 0.01% merthiolate and 1% bovine serum albumin (BSA) was added to the plate at 200 $\mu$l/well, and the plate was kept standing at 4° C. overnight.
(5) The cell extract containing bFGF mutein C86 obtained in Reference Example 3 was diluted with PBS containing 0.1% BSA. From the plate obtained in the above (4), BSA solution was removed, the plate was washed with PBS four times, and the diluted bFGF mutein C86 was added to the plate so as to be 100 $\mu$l/well to adsorb to the plate at 4° C. overnight. The unreacted mutein C86 was removed, and the plate was washed with PBS four times. The monoclonal antibody conjugated with HRP (HRP-MoAb78) obtained in the above (3) was diluted with PBS containing 0.1% BSA to 1/300, and the diluent was added to the plate so as to be 100 $\mu$l/well. The reaction was carried out for 4 hours at room temperature. After removing the antibody, the plate was washed with PBS for 6 times, substrate for oxidase (Bio. Rad Co. U.S.A) was added to the plate so as to be 100 $\mu$l/well. Quantification was accomplished by absorbance measurements at 415 nm, and it was confirmed that a small amount of the mutein C86 was produced.
(6) In FIG. 11, the detection curve is shown in case that the amount of monoclonal antibody MoAb52 which is fixed to the plate is 1 $\mu$g/well ( - - - ○ - - - ), and 2 $\mu$g/well ( - - - ● - - - ). The horizontal axis shows the concentration of bFGF added, and the vertical axis shows the absorbance at 415 nm of the solution caused by HRP-MoAb78.

Figure 11:
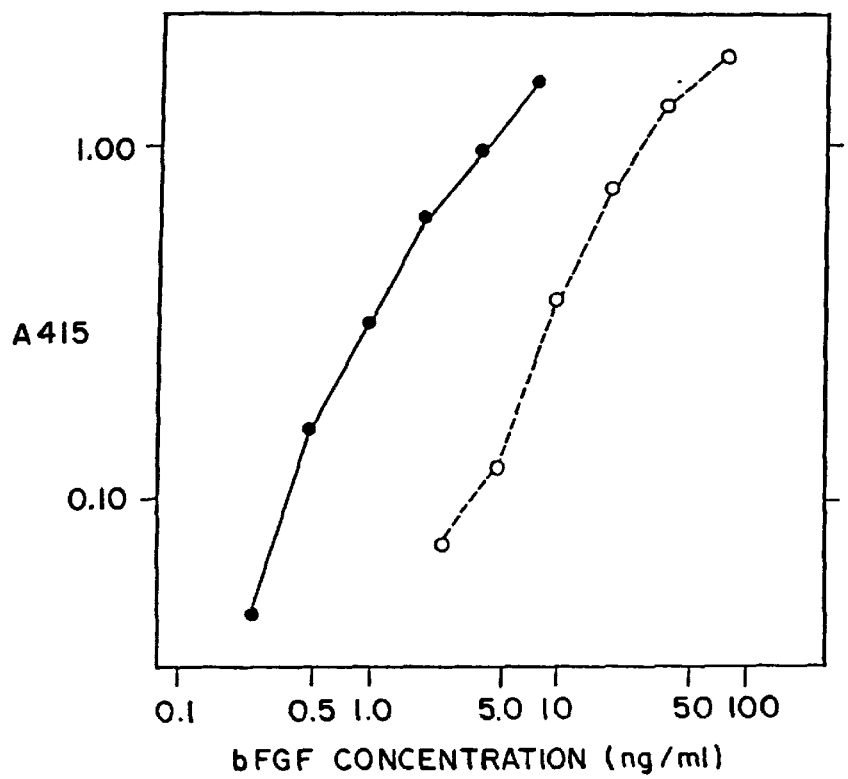
FIG. 11 shows the quantification of bFGF by EIA using MoAb52 and HRP-MoAb78.
Figure 12:
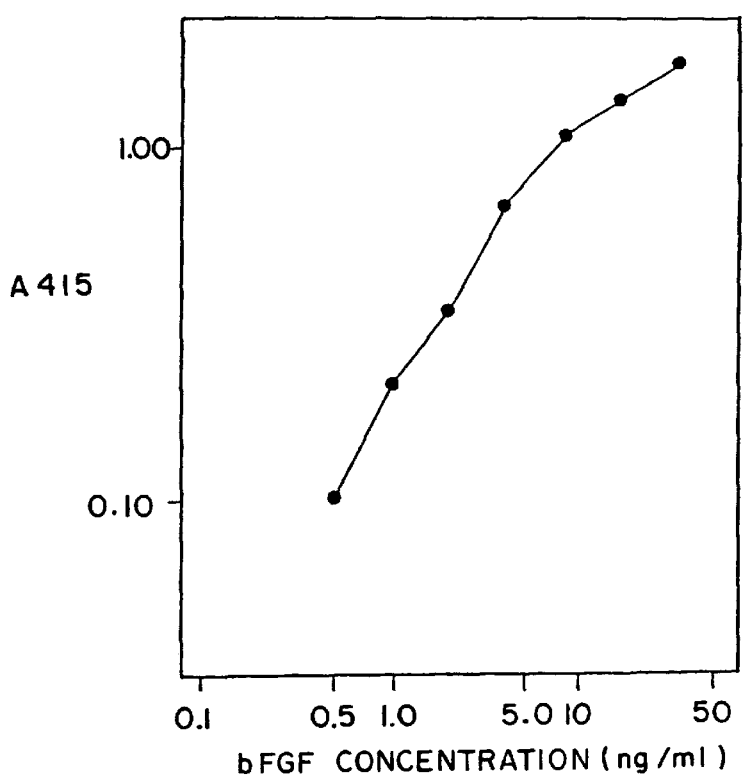
FIG. 12 shows the quantification of bFGF by EIA using MoAb98 and HRP-MoAb78.

From the FIG. 11, it is taught that the concentration of 0.5 ng/ml of bFGF can be detected, when the monoclonal antibody MoAb52 is adsorbed to the plate in an amount of 2 $\mu$g/well.
(7) The monoclonal antibody MoAb98 was adsorbed to the plate in an amount of 2 $\mu$g/well, according to the method of the above (4), and the measurement of absorbance at 415 nm was carried out in accordance with the method of the above (5). The results are shown in FIG. 12. The horizontal and vertical axes show the same as those of FIG. 11. From FIG. 12, it is taught that at least 0.5 ng/ml of bFGF can be detected by using the monoclonal antibody MoAb98.

Example 11

(The measurement of hbFGF mutein by EIA method employing monoclonal antibody)

The cell extract containing human bFGF mutein C86 obtained in Reference Example 13 was treated with the manner of Example 9 to measure the expression amount of the mutein. The results indicate that the mutein C86 is expressed in the cell in a slight amount.

Example 12

(The measurement of hbFGF mutein by EIA method employing monoclonal antibody)

The cell extract containing human bFGF mutein C129 obtained in Reference Example 14 was treated with the manner of Example 9 to measure the expression amount of the mutein. The results indicate that the mutein C129 is expressed in the cell in a slight amount.

Example 13

(Detection of hbFGF by the method of Western blotting)

hbFGF obtained in Reference Example 3 was subjected to electrophoresis employing 17.25% acrylamide gel [Laemmli, Nature, 277, 680–685 (1970)], and it was transferred [Journal of Biochemical and Biophysical Methods, 10, 203–209 (1984)] on the membrane of nitrocellulose by using Sartoblot (Sartorius, West Germany). This membrane was washed with TBS (20 mM Tris.HCl (pH 7.5), 0.5M NaCl] for 5 minutes twice, and kept standing in TBS containing 4% BSA at room temperature for one hour to block the unreacted material on the membrane. Thus obtained membrane was washed with TBS containing 0.05% Tween 20 (TTBS) for 5 minutes twice.

The monoclonal antibody MoAb12 or MoAb78 was diluted with TTBS containing 1% gelatin so as to 1/3000. To thus obtained dilution said nitrocellulose membrane was inserted, and reaction was carried out overnight. After the reaction, the reaction liquid was removed, and the membrane was washed with TTBS for 5 minutes twice.

The secondary antibody, i.e., anti mouse IgG goat serum (Bio Rad, U.S.A.) labeled with HRP, was diluted to 1/3000 by TTBS containing 1% gelatin.

To the membrane obtained above was added the diluted secondary antibody, and reaction was carried out at room temperature for one hour. The membrane thus obtained was washed with TTBS for 5 minutes thrice, and then washed with TBS for 5 minutes twice. After that, to the membrane was added 0.05% 4-chloro-1-naphtol as substrate and 0.015% hydrogen peroxide, and the reaction was carried out for 15 minutes.

Figure 13:
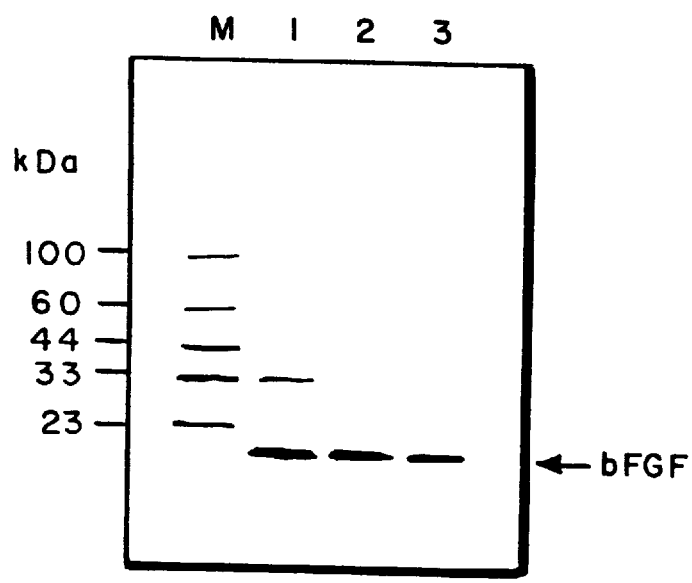
FIG. 13 shows the detection of bFGF by Western blotting method using monoclonal antibody 78 as obtained in Example 12.

In FIG. 13, the results of Western blotting in case the monoclonal antibody MoAb78 was used as primary antibody. The lane 1 shows the results of 1 μg of bFGF, the lane 2 shows the results of 300 μg of bFGF, the lane 3 shows the results of 100 μg of bFGF, wherein bFGF was electrophoresised and transferred. M shows a marker, and the numerals in vertical axis show molecular weight. bFGF was detected in the same sensitivity when the monoclonal antibody MoAb12 instead of MoAb78.

The following references, which are referred to for their disclosures at various points in this application, are incorporated herein by reference.

Nature, 249, 123 (1974)
National Cancer Institute Monograph, 48, 109(1978)
Proceedings of the National Academy of Sciences, U.S.A., 82, 6507(1985)
European Patent Publication No.237,966
European Molecular Biology Organization (EMBO) Journal, 5, 2523(1986)
Genetic Enginnering, Academic Press (1983), pp.31–50
Genetic Enginnering: Principles and Methods, Prenum Press (1981), vol.3, pp.1–32
Journal of Inmunological Methods, 80, 55(1985)
Nature, 256, 495(1975)
Journal of American Medical Association, 199, 549(1967)
Proc. Natl. Acad. Sci. U.S.A., 80, 3513–3516(1983)
Molecular and Cellular Biology, 3, 280(1983)
Nucleic Acids Research 1, 1513(1979)
Proc. Natl. Acad. Sci. U.S.A., 72, 3961(1975)
Nucleic Acids Research, 9, 309(1981)
Nucleic Acids Research, 11, 3077–3085(1983)
Molecular Cloning (1982), A Laboratory Manual, Cold Spring Harbor Laboratory, U.S.A.
Methods in Enzymology, 101, 20–78(1983)
Nature, 227, 680(1970)
Regulatory Peptides, 10, 309–317(1985)
Journal of Biochemical and Biophysical Methods, 10, 203–209(1984)

What we claim is:

1. A monoclonal antibody which specifically binds with basic fibroblast growth factor, wherein the antibody has the following characteristics:
   (a) it has a molecular weight of about 140 to 160 kilodaltons,
   (b) it does not cross-react with acidic fibroblast growth factor,
   (c) it belongs to the immunoglobulin class IgM or IgG, and
   (d) it is capable of detecting human basic fibroblast growth factor in a concentration of at least 0.5 ng/ml of basic fibroblast factor by EIA method.

2. The monoclonal antibody as claimed in claim 1, wherein the basic fibroblast growth factor bound to is a human fibroblast growth factor containing the amino acid sequence:
   Phe-Phe-Leu-Arg-Ile-His-Pro-Asp-Gly-Arg-Val-Asp-Gly-Val-Arg-Glu-Lys-Ser-Asp-Pro.

3. A cloned hybridoma comprising a splenic cell from a mammal immunized with human basic fibroblast growth factor and a homogenic or heterogenic lymphoid cell, wherein the hybridoma is capable of producing a monoclonal antibody which specifically binds with basic fibroblast growth factor, wherein the antibody has the following characteristics:
   (a) it has a molecular weight of about 140 to 160 kilodaltons,
   (b) it does not cross-react with acidic fibroblast growth factor,
   (c) it belongs to the immunoglobulin class IgM or IgG, and
   (d) it is capable of detecting bFGF in the concentration of at least 0.5 ng/ml of basic fibroblast growth factor by EIA method.

4. The cloned hybridoma as claimed in claim 3, wherein the basic fibroblast growth factor is a human fibroblast growth factor containing the amino acid sequence:
   Phe-Phe-Leu-Arg-Ile-His-Pro-Asp-Gly-Arg-Val-Asp-Gly-Val-Arg-Glu-Lys-Ser-Asp-Pro.

* * * * *